United States Patent
Sackler et al.

(10) Patent No.: US 7,740,881 B1
(45) Date of Patent: *Jun. 22, 2010

(54) METHOD OF TREATING HUMANS WITH OPIOID FORMULATIONS HAVING EXTENDED CONTROLLED RELEASE

(75) Inventors: Richard Sackler, Greenwich, CT (US); Robert Kaiko, Weston, CT (US); Paul Goldenheim, Wilton, CT (US)

(73) Assignee: Purdue Pharma LP, Stanford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/624,530

(22) Filed: Jul. 24, 2000

Related U.S. Application Data

(63) Continuation of application No. 08/838,368, filed on Apr. 8, 1997, now Pat. No. 6,143,322, which is a continuation of application No. 08/677,797, filed on Jul. 10, 1996, now abandoned, which is a continuation of application No. 08/561,829, filed on Nov. 27, 1995, now Pat. No. 5,958,459, which is a continuation of application No. 08/086,248, filed on Jul. 1, 1993, now abandoned.

(51) Int. Cl.
*A61K 9/58* (2006.01)
*A61K 9/60* (2006.01)
*A61K 9/36* (2006.01)
*A61K 9/14* (2006.01)
*A61K 9/16* (2006.01)
*A61K 9/62* (2006.01)

(52) U.S. Cl. .................. 424/459; 424/490; 424/458; 424/461; 424/462; 424/495; 424/480; 424/482; 424/497; 514/282

(58) Field of Classification Search .......... 424/459, 424/484, 485, 486, 488, 489
See application file for complete search history.

(56) References Cited

U.S. PATENT DOCUMENTS

| | | | |
|---|---|---|---|
| 2,738,303 A | 3/1956 | Blythe | 167/82 |
| 3,634,584 A | 1/1972 | Poole | 424/21 |
| 3,845,770 A | 11/1974 | Theeuwes et al. | 128/260 |
| 3,870,790 A | 3/1975 | Lowey et al. | 424/19 |
| 3,916,889 A | 11/1975 | Russell | 128/145.8 |
| 3,916,899 A | 11/1975 | Theeuwes et al. | 128/145.8 |
| 4,008,719 A | 2/1977 | Theeuwes et al. | |
| 4,063,064 A | 12/1977 | Saunders et al. | 219/121 |
| 4,088,864 A | 5/1978 | Theeuwes et al. | |
| 4,132,753 A | 1/1979 | Blichare et al. | 264/75 |
| 4,377,568 A | 3/1983 | Chopra | 424/31 |
| 4,385,078 A | 5/1983 | Onda et al. | 427/3 |
| 4,389,393 A | 6/1983 | Schor et al. | 424/19 |
| 4,421,736 A | 12/1983 | Walters | 424/19 |
| 4,443,428 A | 4/1984 | Oshlack | 424/22 |
| 4,464,378 A | 8/1984 | Hussain | 424/260 |
| 4,483,847 A | 11/1984 | Augart | 424/22 |
| 4,520,172 A | 5/1985 | Lehmann et al. | 525/369 |
| 4,548,990 A | 10/1985 | Mueller et al. | 525/123 |
| 4,557,925 A | 12/1985 | Lindahl et al. | 424/19 |
| 4,600,645 A | 7/1986 | Ghebre-Sellassie et al. | 428/403 |
| 4,609,542 A | 9/1986 | Panoz et al. | 424/498 |
| 4,708,874 A | 11/1987 | De Haan et al. | 424/470 |
| 4,728,513 A | 3/1988 | Ventouras | 424/461 |
| 4,797,410 A | 1/1989 | El-Fakahany | 514/356 |
| 4,806,337 A | 2/1989 | Snipes et al. | 71/65 |
| 4,828,836 A | 5/1989 | Elger et al. | 424/419 |
| 4,834,984 A | 5/1989 | Goldie et al. | 424/488 |
| 4,834,985 A | 5/1989 | Elger et al. | 424/488 |
| 4,844,907 A | 7/1989 | Elger et al. | 424/465 |
| 4,844,909 A | 7/1989 | Goldie et al. | 424/480 |
| 4,861,598 A | 8/1989 | Oshlack | 424/468 |
| 4,894,234 A | 1/1990 | Sharma et al. | 424/440 |
| 4,935,246 A | 6/1990 | Ahrens | 424/490 |

(Continued)

FOREIGN PATENT DOCUMENTS

AU 9047732 7/1990

(Continued)

OTHER PUBLICATIONS

Abraham Sunshine, et al., "Analgesic oral efficacy of tramadol hydrochloride in postoperative pain," *Clin. Pharmacol. Ther.*, Jun. 1992, pp. 740-746.

(Continued)

*Primary Examiner*—Yong S Chong
(74) *Attorney, Agent, or Firm*—Davidson, Davidson & Kappel, LLC

(57) ABSTRACT

Solid controlled-release oral dosage forms comprising a therapeutically effective amount of an opioid analgesic or a salt thereof which provide an extended duration of pain relief of about 24 hours, have a dissolution rate in-vitro of the dosage form, when measured by the USP Paddle Method at 100 rpm at 900 ml aqueous buffer (pH between 1.6 and 7.2) at 37° C. of from about 12.5% to about 42.5% (by wt) opioid released after 1 hour, from about 25% to about 65% (by wt) opioid released after 2 hours, from about 45% to about 85% (by wt) opioid released after 4 hours, and greater than about 60% (by wt) opioid released after 8 hours, the in-vitro release rate being substantially independent of pH and chosen such that the peak plasma level of said opioid analgesic obtained in-vivo occurs from about 2 to about 8 hours after administration of the dosage form.

23 Claims, 6 Drawing Sheets

U.S. PATENT DOCUMENTS

| | | | | |
|---|---|---|---|---|
| 4,957,745 | A | 9/1990 | Jonsson et al. | |
| 4,970,075 | A | 11/1990 | Oshlack | 424/451 |
| 4,983,730 | A | 1/1991 | Domeshek et al. | 536/69 |
| 4,990,341 | A | 2/1991 | Goldie et al. | 424/484 |
| 5,007,790 | A | 4/1991 | Shell | 424/451 |
| 5,019,397 | A | 5/1991 | Wong et al. | 424/473 |
| 5,023,089 | A | 6/1991 | Sakamoto et al. | 424/490 |
| 5,024,842 | A | 6/1991 | Edgren et al. | 424/473 |
| 5,026,560 | A | 6/1991 | Makino et al. | 424/494 |
| 5,030,400 | A | 7/1991 | Danielsen et al. | 264/101 |
| 5,068,110 | A | 11/1991 | Fawzi et al. | 424/461 |
| 5,071,646 | A | 12/1991 | Malkowska | 424/497 |
| 5,122,384 | A | 6/1992 | Paradissis et al. | 424/451 |
| 5,126,145 | A | 6/1992 | Evenstad et al. | 424/465 |
| 5,132,142 | A | 7/1992 | Jones et al. | 247/196 |
| 5,133,974 | A | 7/1992 | Paradissis et al. | 424/480 |
| 5,167,964 | A | 12/1992 | Muhammed et al. | 424/482 |
| 5,169,645 | A | 12/1992 | Shukla et al. | 424/499 |
| 5,178,866 | A | 1/1993 | Wright et al. | |
| 5,178,868 | A | 1/1993 | Malmqvist-Granlund et al. | 424/490 |
| 5,196,203 | A | 3/1993 | Boehm | 424/469 |
| 5,202,128 | A | 4/1993 | Morella et al. | 424/469 |
| 5,206,030 | A | 4/1993 | Wheatley et al. | 424/490 |
| 5,219,575 | A | 6/1993 | Bommel et al. | 424/490 |
| 5,248,516 | A | 9/1993 | Wheatley et al. | 427/214 |
| 5,258,436 | A | 11/1993 | Wheatley et al. | 524/388 |
| 5,266,331 | A | 11/1993 | Oshlack et al. | 424/468 |
| 5,273,760 | A | 12/1993 | Oshlack et al. | 424/480 |
| 5,283,065 | A | 2/1994 | Doyon et al. | 424/467 |
| 5,286,493 | A * | 2/1994 | Oshlack et al. | 424/468 |
| 5,292,461 | A | 3/1994 | Juch et al. | 264/37 |
| 5,292,522 | A | 3/1994 | Petereit et al. | |
| 5,321,012 | A | 6/1994 | Mayer et al. | 514/25 |
| 5,330,766 | A | 7/1994 | Morella et al. | 424/490 |
| 5,378,474 | A | 1/1995 | Morella et al. | 424/469 |
| 5,384,130 | A | 1/1995 | Kamada | 424/461 |
| 5,411,745 | A | 5/1995 | Oshlack et al. | 424/456 |
| 5,456,923 | A | 10/1995 | Nakamichi et al. | 424/489 |
| 5,460,826 | A | 10/1995 | Merrill et al. | 424/470 |
| 5,472,712 | A | 12/1995 | Oshlack et al. | 424/480 |
| 5,478,577 | A * | 12/1995 | Sackler et al. | 424/489 |
| 5,500,227 | A | 3/1996 | Oshlack et al. | 424/476 |
| 5,502,058 | A | 3/1996 | Mayer et al. | 514/289 |
| 5,508,042 | A | 4/1996 | Oshlack et al. | 424/468 |
| 5,520,931 | A | 5/1996 | Persson et al. | 424/473 |
| 5,549,912 | A | 8/1996 | Oshlack et al. | 424/468 |
| 5,580,578 | A | 12/1996 | Oshlack et al. | 424/468 |
| 5,593,695 | A | 1/1997 | Merrill et al. | 424/480 |
| 5,601,842 | A | 2/1997 | Bartholomaeus | 424/464 |
| 5,614,218 | A | 3/1997 | Olsson | 424/456 |
| 5,629,011 | A | 5/1997 | Illum | 242/434 |
| 5,637,320 | A | 6/1997 | Bourke et al. | 424/484 |
| 5,656,295 | A | 8/1997 | Oshlack et al. | 424/468 |
| 5,667,805 | A | 9/1997 | Merrill et al. | 424/473 |
| 5,670,172 | A | 9/1997 | Buxton et al. | 424/495 |
| 5,672,360 | A * | 9/1997 | Sackler et al. | 424/490 |
| 5,681,585 | A | 10/1997 | Oshlack et al. | 424/494 |
| 5,843,480 | A | 12/1998 | Miller et al. | 424/484 |
| 5,849,240 | A | 12/1998 | Miller et al. | 264/460 |
| 5,879,705 | A | 3/1999 | Heafield et al. | 424/464 |
| 5,891,471 | A | 4/1999 | Miller et al. | 424/468 |
| 5,965,163 | A | 10/1999 | Miller et al. | 424/468 |
| 5,968,551 | A | 10/1999 | Oshlack et al. | 424/456 |
| 6,143,322 | A * | 11/2000 | Sackler et al. | 424/459 |

FOREIGN PATENT DOCUMENTS

| | | |
|---|---|---|
| AU | 9341654 | 2/1995 |
| CA | 2082573 | 11/1992 |
| CA | 2131350 A1 | 1/1994 |
| EP | 0097523 | 1/1984 |
| EP | 0108218 A2 | 5/1984 |
| EP | 0147780 A2 | 7/1985 |
| EP | 0235986 A1 | 9/1987 |
| EP | 0253104 A1 | 1/1988 |
| EP | 0327295 | 1/1989 |
| EP | 0361910 A1 | 4/1990 |
| EP | 0377517 A2 | 4/1990 |
| EP | 0377518 A2 | 7/1990 |
| EP | 0388954 A2 | 9/1990 |
| EP | 0415693 A1 | 3/1991 |
| EP | 0452145 A2 | 10/1991 |
| EP | 0532348 A2 | 3/1993 |
| EP | 0533297 A1 | 3/1993 |
| EP | 0534628 A1 | 3/1993 |
| EP | 0535841 A1 | 4/1993 |
| EP | 0546676 A1 | 6/1993 |
| EP | 0548448 A1 | 6/1993 |
| EP | 0553392 A1 | 8/1993 |
| EP | 0580860 A1 | 2/1994 |
| EP | 636370 A1 | 6/1994 |
| EP | 0636370 A1 | 6/1994 |
| EP | 0361680 B1 | 7/1994 |
| EP | 0609961 A1 | 8/1994 |
| EP | 0430287 B1 | 10/1994 |
| EP | 0636370 A1 | 1/1995 |
| EP | 0665010 A1 | 8/1995 |
| EP | 0377518 B1 | 2/1996 |
| EP | 0267702 A3 | 5/1998 |
| EP | 0271193 | 6/1998 |
| GB | 2053681 B | 1/1981 |
| GB | 2178313 A | 2/1987 |
| GB | 2170104 | 7/1988 |
| JP | 0166608 | 8/1995 |
| WO | WO9201446 | 2/1992 |
| WO | WO9202209 A1 | 2/1992 |
| WO | WO9206679 | 4/1992 |
| WO | WO9208459 | 5/1992 |
| WO | WO9304675 | 3/1993 |
| WO | WO9307859 A1 | 4/1993 |
| WO | WO9307861 | 4/1993 |
| WO | WO9310765 | 6/1993 |
| WO | WO9318753 | 9/1993 |
| WO | WO9403160 | 2/1994 |
| WO | WO9403161 | 2/1994 |
| WO | WO9405262 | 3/1994 |
| WO | WO9422431 | 10/1994 |
| WO | WO9600066 | 1/1996 |
| WO | WO9601629 | 1/1996 |
| WO | WO9614058 | 3/1996 |

OTHER PUBLICATIONS

E. Beubler, "Medikamentose Schmerztherapie: Kriterien, Moglichkeiten, Risken," *Therapiewoche Osterreich*, 7, 2 (1992), pp. 90-96, with English translation.

Geoffrey K. Gourlay, Ph.D., et al., "Influence of a high-fat meal on the absorption of morphine from oral solutions," *Clin. Pharmacol. Ther.*, Oct. 1989, pp. 463-468.

Robert Kaiko, et al., "A Single-Dose Study of the Effect of Food Ingestion-And Timing of Dose Administration on the Pharmacokinetic Profile of 30-MG Sustained-Release Morphine Sulfate Tablets," *Current Therapeutic Research*, vol. 47, No. 5, May 1990, pp. 869-878.

Geoffrey K. Gourlay, Ph.D., "The Reproducibility of Bioavailability of Oral Morphine from Solution Under Fed and Fasted Conditions," *Journal of Pain and Symptom Management*, vol. 6., No. 7, Oct. 1991, pp. 431-436.

Robert F. Kaiko, et al., "Controlled-Release Morphine Bioavailability (MS Contin Tablets) in the Presence and Absence of Food," *The Hospice Journal*, vol. 6(4) 1990, pp. 17-30.

N. Yokokawa, et al., "Relationship between plasma concentration of morphine and analgesic effectiveness," *Postgrad Med J*, (1991) 67 (Suppl. 2) pp. 550-554.

Physicians Desk Reference 1994, 48th Edition, pp. 1821-1824.

D.L. Munday, "Changes in Drug Release Rate 2, Effect of Temperature and Relative Humidity on Polymeric Film Coatings," 5th Cong. Int. Tech. Pharm., 1989, vol. 2, pp. 55-60.

A Protocol for a clinical study entitled "A Randomized, Double-Blind, Parallel-Group Study comparing the Efficacy and Safety of Kapanol® to MsContin® in the Management of Patients with Moderate to Severe Cancer Pain" ("the Protocol"). The date of the Protocol is indicated as Feb. 10, 1992 and it bears COD No. 14556. The sponsor of the study is indicated to be Faulding Pharmaceuticals, an Australian company.

Certain Patient Diary Cards, Drug Disposition Records, Case Reports Forms and a listing which apparently correlates patient randomization number with the treatment of dosing regimen assigned to each patient.

Patient consent forms, apparently for four study participants.

Certain documents regarding Institutional Review Board Approval for the Faulding-sponsored study.

Investigator Agreements between the study organizers and certain of the principal investigators.

Abstracts from the Twelfth Annual Congress of the Oncology Nursing Society, May 1987.

J. Lapin et al., "Cancer Pain Management with a Controlled Release Oral Morphine Preparation," *Journ. Of Pain and Sympton Manag.*, v 4 (3), pp. 146-151, 1989.

J. Lapin et al., "Guidelines for use of Controlled Release Oral Morphine in Cancer pln Management," *Cancer Nursing*, v 12 (4), pp. 202-208, 1989.

R.F. Kaiko, "The Pre-and Postoperative Use of Controlled-Release Morphine (MS Contin Tablets): A Review of the Published Literature," Medical Department, The Purdue Frederick Company, Royal Society of Medical Services, International Congress, Symposium Services, No. 149, pp. 147-160 (1989).

H.F. Slowey et al., "Effect of Premedication with Controlled-Release Oral Morphine on Postoperative Pain," Anaesthesia, 1985, vol. 40, pp. 438-440.

MS Contin—Frequency of Daily Dosing, Jan.-Nov. 1990.

R.K. Portenoy, et al., "A Randomized, Double-Blind, Double-Dummy, Crossover Study Comparing the Pharmacokinetics and Pharmacodynamics of Kapanol® Capsules Given Every 24 hours and Every 12 hours with MS Contin® Tablets Given Every 12 Hours in the Management of Patients with Moderate to Severe Chronic Pain".

R. West et al., World Congress on Pain Abstracts 997-1001, Aug. 26, 1993.

Advertisement: Rosanol SR., 1988 Roxane Labs, Inc.

R. Kaiko and T. Hunt, Clip. Thera. vol. 13, No. 4, pp. 484-488, 1991.

S. Bloomfield, et al. Clin. Pharmacol. Ther. vol. 53, No. 4, pp. 469-478, 1993.

Advertisement: MS Contin 1986, 1987 The Purdue Frederick Company.

Sustained Release Medications, Noyes Data Corp., pp. 3,4, 10-15, 96-99, 335-337 (1980).

Flanders, P., et al., "The Control of Drug Release From Conventional Melt Granulation Matrices," *Drug Development and Industrial Pharmacy*, vol. 13, No. 6, pp. 1001-1022 (1987).

McTaggart, Celia M., et al., "The evaluation of formulation and processing conditions of a melt granulation process," *International Journal of Pharmaceutics*, vol. 19, pp. 139-148 (1984).

Schaefer, T., et al., "Melt granulation in a laboratory scale high shear mixer," *Drug Development and Industrial Pharmacy*, vol. 16, No. 8.\, pp. 1249-1277 (1990).

Thomsen, L.. Juul, et al., "Prolonged Release Matrix Pellets Prepared by Melt Pelletization I. Process Variables," *Drug Development and Industrial Pharmacy*, vol. 19, No. 15, pp. 1867-1887 (1993).

Thomsen, L.. Juul, et al., "Prolonged Release Matrix Pellets prepared by Melt Pelletization II. Hydrophobic Substances as Meltable Binders," *Drug Development and Industrial Pharmacy*, vol. 20, No. 77, pp. 1179-1197 (1994).

Thomsen, L.. Juul, "Utilizing melt pelletization technique for the preparation of prolonged release products," *Pelletization*, (material elaborated by assistant prof. Lars Juul Thomsen, Department of Pharmaceutics, Royal Danish School of Pharmacy for the DIE course "Pelletization Technologh," Nov. 1992, 106 pages plus 3 appendices.

Thomsen, L.. Juul, "Prolonged Release Matrix Pellets Prepared by Melt Pelletization. Part IV: Drug Particles Size, and Binder Composition," *Pharmaceutical Technology Europa*, pp. 19-24 (Oct. 1994).

Maccarrone C. et al.; Single Dose Pharmacokinetics of Kapanol™, a New Oral Sustained-Release Morphine Formulation; Clinical Drug Investigation 1994:7 (5) 262-274.

West R. J. Maccarrone C. Single dose pharmacokinetics of a new oral sustained release morphine formulation, Kapanol™ capsules. (Abstract 997) International Association for the Study of Pain, 7th World Congress on Pain. Paris, Aug. 22-27, 1993 (Data on file, Glaxo Australia, F.H. Faulding).

Gourlay GK, Plummer JL, Cherry DA, et al. A comparison of Kapanol™ (A new sustained release morphine formulation), MST Continus® and morphine solution in cancer patients: pharmacokinetic aspects. (Abstract 998) International Association for the Study of Pain, 7th World Congress on Pain. Paris, Aug. 22-27; 1993 (Data on file, Glaxo Australia, F.H. Faulding).

Cherry DA, Gourley GK, Plummer JL, et al. A comparison of Kapanol™ (a new sustained release morphine formulation), MST Continus® and morphine solution in cancer patients: morphine metabolite profiles and renal function. (Abstract 999) International Association for the Study of Pain, 7th World Congress on Pain, Paris, Aug. 22-27, 1993 (Data on file, Glaxo Australia, F.H. Faulding).

Plummer JL, Cherry DA, Gourlay GK, et al. A comparison of Kapanol™ (a new sustained release morphine formulation) MST Continus® and morphine solution in cancer patients: pharmacodynamic aspects. (Abstract 1000) International Association for the Study of Pain, 7th World Congress on Pain, Paris, Aug. 22-27, 1993 (Data on file, Glaxo Australia, F.H. Faulding).

Toner G, Cramond T, Bishop, et al. Randomized double blind, phase III crossover study of a new sustained-release oral morphine formulation, Kapanol™ capsules, (Abstract 1001) International Association for the Study of Pain, 7th World Congress on Pain, Paris, Aug. 22-27, 1993 (Data on file, Glaxo Australia, F.H. Faulding).

European Journal of Cancer, Once a Day (i.e. 24 Hourly) Kapanol™, A New Sustained Release Morphine Formulation, in the Treatment of Cancer Pain: Morphine Metabolite Profiles; Part A General Topics 1995; 31 (S5) Suppl:S184 Abs 884, European Conference on Clinical Oncology and Cancer Nursing, Paris, Oct. 29-Nov. 2, 1995.

European Journal of Cancer; Once a Day (i.e. 24 Hourly) Kapanol™, A New Sustained Release Morphine Formulation, In The Treatment of Cancer Pain: Pharmacokinetic Aspects; Part A General Topics 1995:31 (S5) Suppl: S187 Abs 897 European Conference on Clinical Oncology and Cancer Nursing, Paris, Oct. 29-Nov. 2, 1995.

European Journal of Cancer; Kadian™/Kapanol™-A Once Daily Morphine Formulation; Part A-General Topics 1995;31 (S5) Suppl: S182 Abs 873 European Conference on Clinical Oncology and Cancer Nursing, Paris, Oct. 29-Nov. 2, 1995.

Gourlay et al., Proceeding of the 7th World Congress on Pain; A comparison of Kapanol (a New Sustained-Release Morphine Formulation), MST Continus, and Morphine Solution in Cancer Patients: Pharmacokinetic Aspects of Morphine and Morphine Metabolites Progress In Pain Research and Management vol. 2 pp. 631-643.

Kaiko R.F.; Cinical Protocol and Role of Controlled Release Morphine in the Surgical Patient; Anesthesiology and Pain Management 1991 pp. 193-212.

MS Contin—Frequency of Daily Dosing (NDTI)—Jun. 1991-May 1992.

* cited by examiner

METHOD OF TREATING HUMANS WITH OPIOID FORMULATIONS HAVING EXTENDED CONTROLLED RELEASE

This application is a continuation of U.S. patent application Ser. No. 08/838,368, filed Apr. 8, 1997 now U.S. Pat. No. 6,143,322, the disclosure of which is hereby incorporated by reference, which is a continuation of U.S. patent application Ser. No. 08/677,797, filed Jul. 10, 1996, now abandoned, which is a continuation of U.S. patent application Ser. No. 08/561,829, filed Nov. 27, 1995, now U.S. Pat. No. 5,958,459, issued Sep. 28, 1999, which is a continuation of U.S. patent application Ser. No. 08/086,248, filed Jul. 1, 1993, now abandoned.

BACKGROUND OF THE INVENTION

The present invention relates to a solid, controlled-release oral dosage form for use in the treatment of pain.

It is the intent of all controlled (slow) release formulations to provide a longer period of pharmacologic action after administration than is ordinarily obtained after administration of immediate-release dosage forms. Such longer periods of response provide for many therapeutic benefits that are not achieved with corresponding short acting, immediate release preparations. Thus, therapy may be continued without interrupting the sleep of the patient, which is of special importance, for example, when treating a patient for moderate to severe pain (e.g., a post-surgery patient, a cancer patient, etc.), or for those patients who experience migraine headaches on awakening, as well as for the debilitated patient for whom sleep is essential.

Unless conventional rapid acting drug therapy is carefully administered at frequent intervals to maintain effective steady state blood levels of the drug, peaks and valleys in the blood level of the active drug occurs because of the rapid absorption, systemic excretion of the compound and through metabolic in-activation, thereby producing special problems in maintenance therapy of the patient. A further general advantage of longer acting drug preparations is improved patient compliance resulting from the avoidance of missed doses through patient forgetfulness.

Morphine, which is considered to be the prototypic opioid analgesic, has been formulated into 12 hour controlled-release formulations (i.e., MS Contin® tablets, commercially available from Purdue Frederick Company).

It has previously been known in the art that controlled-release compositions of opioids or salts thereof could be prepared in a suitable matrix. For example, in U.S. Pat. Nos. 4,990,341 and 4,844,909 (Goldie, et al.), both assigned to the assignee of the present invention, describes hydromorphone compositions wherein the dissolution rate in-vitro of the dosage form, when measured by the USP Paddle or Basket Method at 100 rpm in 900 ml aqueous buffer (pH between 1.6 and 7.2) at 37° C., is between 12.5 and 42.5% (by wt) hydromorphone released after 1 hour, between 25 and 55% (by wt) released after 2 hours, between 45 and 75% (by wt) released after 4 hours and between 55 and 85% (by wt) released after 6 hours, the in-vitro release rate being independent of pH between pH 1.6 and 7.2 and chosen such that the peak plasma level of hydromorphone obtained in-vivo occurs between 2 and 4 hours after administration of the dosage form. At least 12 hours of pain relief is obtained with these hydromorphone formulations.

It has been a further goal in the art to develop drug formulations which provide a duration of effect longer than 12 hours, so that, for example, the drug may be administered to the patient only once a day.

There is clearly a need for convenient and reliable dosage formulations of opioid analgesics that can be administered less frequently than currently available such drugs. Most currently available such oral opioid analgesic formulations need to be administered every four to six hours with only a selected few formulated for less frequent 12 hour dosing. The obvious advantages for once daily dosing formulations would be both increased convenience and compliance, as have been documented for numerous medication formulations when the requirement for less frequent dosing is provided.

To date, it has not been the consensus that the formulation of oral opioid analgesics in a way that provides for less frequent dosing either (a) has any influence on the profile and/or incidence of adverse drug reactions as compared to the same chemical entity administered in conventional immediate-release oral formulations at the same total daily dose or (b) that there are any differences in the analgesic efficacy of longer as compared to shorter acting oral opioid analgesic formulations in terms of the dosage required over given periods of time. The results of numerous adequate and well-controlled double-blind, randomized, safety and efficacy evaluations demonstrate comparable profiles, incidences and intensities of opioid side effects and comparable analgesia at equal daily dosages of long- and shorter-acting oral opioids as evidenced from the results of numerous such studies.

While the concurrent administration of non-opioid analgesic drugs along with opioid drugs have provided for evidence of the "opioid-sparing" effect of non-opioid analgesics, the only previously reported method of decreasing opioid requirements have been in the situation where patient-controlled analgesia (PCA) reduces the need for opioid analgesics as compared to when administered as-needed (PRN), both via parenteral routes. In these latter situations, neither method of administration is at fixed intervals but, rather, PRN, with the patient as the primary controller of drug administration utilizing PCA and both the patient and another party, who controls the timing of as-needed but PRN medication in the usual fashion.

It is an object of the present invention to provide a method and opioid analgesic formulation for substantially improving the efficiency and quality of pain management.

It is another object of the present invention to provide a method of treatment for substantially improving the efficiency and quality of pain management.

It is yet another object of the present invention to provide controlled-release opioid formulations which have a substantially increased duration of effect as compared to previously known controlled-release opioid formulations.

SUMMARY OF THE INVENTION

The above objects and others are attained by virtue of the present invention, which is related to a solid controlled-release oral dosage form, the dosage form comprising a therapeutically effective amount of analgesic, preferably an opioid analgesic or a salt thereof, coated with a controlled-release coating or in a controlled-release matrix wherein the dissolution rate in-vitro of the dosage form, when measured by the USP Paddle or Basket Method at 100 rpm in 900 ml aqueous buffer (pH between 1.6 and 7.2) at 37° C. is from about 12.5 to about 42.5% (by wt) opioid released after 1 hour, from about 25 to about 56% (by wt) opioid released after 2 hours, from about 45 to about 85% (by wt) opioid released after 4 hours, and greater than about 60% (by wt) opioid released after 8 hours, the in-vitro release rate being substantially independent of pit, such that the peak plasma level of opioid obtained in-vivo occurs from about 2 to about 8 hours after administration of the dosage form. The oral dosage forms of the present invention provide pain relief for about 24 hours, and therefore may be administered on a once-a-day basis.

As stated above, the dosage form preferably contains an opioid analgesic. Preferred opioids include mu-agonist opioid analgesics such as hydromorphone, oxycodone, morphine, levorphanol, methadone, meperidine, heroin, dihydrocodeine, codeine, dihydromorphine, buprenorphine, salts thereof, mixtures of any of the foregoing, mixed mu-agonists/antagonists, mu-agonist/antagonist combinations, and the like.

USP Paddle or Basket Method is the Paddle and Basket Method described, e.g., in U.S. Pharmacopoeia XXII (1990).

In the present specification, "substantially independent of pH" means that the difference, at any given time, between the amount of opioid released at, e.g., pH 1.6, and the amount released at any other pH, e.g., pH 7.2 (when measured in-vitro using the USP Paddle or Basket Method at 100 rpm in 900 ml aqueous buffer), is 10% (by weight) or less. The amounts released being, in all cases, a mean of at least three experiments.

The present invention is also related to a method of treating pain in a human patient, comprising administering the oral dosage forms of the present invention.

The controlled-release oral solid dosage forms of the present invention provide the surprising result that these formulations may be opioid-sparing. First, it is possible that the controlled-release oral solid dosage forms of the present invention may be dosed at a substantially lower daily dosage in comparison to conventional immediate-release products, with no difference in analgesic efficacy. Second, at comparable daily dosages, greater efficacy may result with the use of the controlled-release oral solid dosage forms of the present invention in comparison to conventional immediate-release products.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
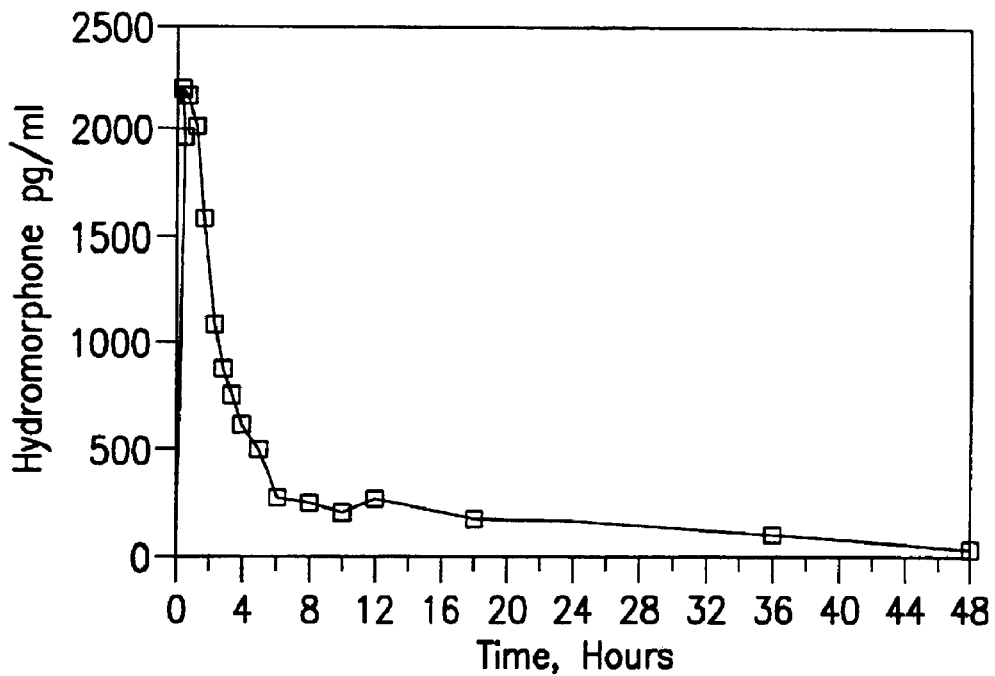
FIG. 1 is a graphical representation of the plasma levels obtained when 2 tablets of Dilaudid® 4 mg tablets are administered.

The invention is based partly upon the surprising discovery that controlled-release dosage forms of opioid analgesics having an extended duration of therapeutic effect, e.g., about 24 hours, provide a peak plasma level (i.e., $t_{max}$) from about 2 to about 8 hours after administration, and preferably provide a peak plasma level from about 4 to about 6 hours after administration, thereby providing pain relief well beyond 12 hours, and preferably, for about 24 hours after oral administration.

Furthermore, in the case of the present dosage form, therapeutic levels are generally achieved substantially without significant increases in the intensity and/or degree of concurrent side effects, such as nausea, vomiting, or drowsiness, which are often associated with high blood levels of opioids. There is also evidence to suggest that the use of the present dosage forms leads to a reduced risk of drug addiction.

A further advantage of the present composition, which releases the opioid analgesic at a rate that is independent of pH, e.g., between pH 1.6 and 7.2, is that it avoids "dose dumping" upon oral administration:

For the first time, oral opioid analgesics have been formulated to provide for an increased duration of analgesic action allowing once-daily dosing. Surprisingly, these formulations, at comparable daily dosages of conventional immediate-release drug, are associated with a lower incidence in severity of adverse drug reactions and can also be administered at a lower daily dose than conventional oral medication while maintaining pain control. Thus, the 24 hour dosing formulations of the present invention can be "opioid-sparing".

The present oral dosage form may be presented as, for example, granules, spheroids or pellets in a capsule or in any other suitable solid form. In one especially preferred embodiment, the oral dosage form comprises an effective number of spheroids contained within a capsule.

In one preferred embodiment, the controlled-release opioid oral dosage form of the present invention includes hydromorphone as the therapeutically active ingredient, and preferably contains from about 4 to about 64 mg hydromorphone hydrochloride. Alternatively, the dosage form may contain molar equivalent amounts of other hydromorphone salts or of the hydromorphone base. In other preferred embodiments where the opioid analgesic is other than hydromorphone, the dosage form contains an appropriate amount to provide a substantially equivalent therapeutic effect.

For example, when the opioid analgesic comprises morphine, the controlled release oral dosage forms of the present invention include form about 15 mg to about 800 mg morphine, by weight.

On the other hand, when the opioid analgesic comprises oxycodone, the controlled release oral dosage forms of the present invention include from about 10 mg to about 400 mg oxycodone.

A review of dose-response studies and relative analgesic assays of mu-agonist opioid analgesics all indicate no significant deviation from parallelism in their dose-response relationships. This is so well-established that it has become an underlining principal providing for establishing relative analgesic potency factors and dose ratios which are commonly utilized when converting patients from one mu-agonist analgesic to another regardless of the dosage of the former.

In one preferred embodiment of the present invention, the controlled-release dosage form comprises spheroids containing the active ingredient coated with a controlled-release coating. The term spheroid is known in the pharmaceutical art and means, e.g., a spherical granule having a diameter of between 0.1 mm and 2.5 mm, especially between 0.5 mm and 2 mm.

The spheroids are preferably film coated with a material that permits release of the opioid (or salt) at a controlled rate in an aqueous medium. The film coat is chosen so as to achieve, in combination with the other stated properties, the in-vitro release rate outlined above (between 12.5% and 42.5% (by wt) release after 1 hour, etc.). The coating formulations of the present invention should be capable of producing a strong, continuous film that is smooth and elegant, capable of supporting pigments and other coating additives, non-toxic, inert, and tack-free.

In one preferred embodiment, the present invention is related to a stabilized solid controlled dosage form comprising an opioid coated with a hydrophobic polymer selected from (i) ethylcellulose; (ii) an acrylic polymer; or (iii) mixtures thereof.

In further preferred embodiments, the coating is derived from an aqueous dispersion of the hydrophobic polymer. The coated substrate containing the opioid(s) (e.g., a tablet core or inert pharmaceutical beads or spheroids) is then cured until an endpoint is reached at which the substrate provides a stable dissolution. The curing endpoint may be determined by comparing the dissolution profile (curve) of the dosage form immediately after curing to the dissolution profile (curve) of the dosage form after exposure to accelerated storage conditions of, e.g., at least one month at a temperature of 40° C. and a relative humidity of 75%. These formulations are described in detail in the assignee's co-pending U.S. application Ser. Nos. 07/814,111 and 07/826,084, hereby incorporated by reference.

The aqueous dispersions of hydrophobic polymers used as coatings in the present invention may be used in conjunction with tablets, spheroids (or beads), microspheres, seeds, pellets, ion-exchange resin beads, and other multi-particulate systems in order to obtain a desired controlled-release of the therapeutically active agent. Granules, spheroids, or pellets, etc., prepared in accordance with the present invention can be presented in a capsule or in any other suitable dosage form.

In order to obtain a controlled-release formulation, it is usually necessary to overcoat the substrate comprising the therapeutically active agent with a sufficient amount of the aqueous dispersion of e.g., ethylcellulose or acrylic polymer, to obtain a weight gain level from about 2 to about 25 percent, although the overcoat may be lesser or greater depending upon the physical properties of the therapeutically active agent and the desired release rate, the inclusion of plasticizer in the aqueous dispersion and the manner of incorporation of the same, for example.

Although ethylcellulose is one preferred hydrophobic polymer which may be used for coating the substrates of the present invention, those skilled in the art will appreciate that other cellulosic polymers, including other alkyl cellulosic polymers, may be substituted for part or all of the ethylcellulose included in the hydrophobic polymer coatings of the present invention.

In other preferred embodiments of the present invention, the hydrophobic polymer comprising the controlled-release coating is a pharmaceutically acceptable acrylic polymer, including but not limited to acrylic acid and methacrylic acid copolymers, methacrylic acid copolymers, methyl methacrylate copolymers, ethoxyethyl methacrylates, cyanoethyl methacrylate, methyl methacrylate, copolymers, methacrylic acid copolymers, methyl methacrylate copolymers, methyl methacrylate copolymers, methyl methacrylate copolymers, methacrylic acid copolymer, aminoalkyl methacrylate copolymer, methacrylic acid copolymers, methyl methacrylate copolymers, poly(acrylic acid), poly(methacrylic acid, methacrylic acid alkylamide copolymer, poly(methyl methacrylate), poly(methacrylic acid) (anhydride), methyl methacrylate, polymethacrylate, methyl methacrylate copolymer, poly(methyl methacrylate), poly(methyl methacrylate) copolymer, polyacrylamide, aminoalkyl methacrylate copolymer, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In order to obtain a desirable dissolution profile, it may be necessary to incorporate two or more ammonio methacrylate copolymers having differing physical properties, such as different molar ratios of the quaternary ammonium groups to the neutral (meth)acrylic esters.

In embodiments of the present invention where the coating comprises an aqueous dispersion of a hydrophobic polymer, the inclusion of an effective amount of a plasticizer in the aqueous dispersion of hydrophobic polymer will further improve the physical properties of the film. For example, because ethylcellulose has a relatively high glass transition temperature and does not form flexible films under normal coating conditions, it is necessary to plasticize the ethylcellulose before using the same as a coating material. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Examples of suitable plasticizers for ethylcellulose include water insoluble plasticizers such as dibutyl sebacate, diethyl phthalate, triethyl citrate, tributyl citrate, and triacetin, although it is possible that other water-insoluble plasticizers (such as acetylated monoglycerides, phthalate esters; castor oil, etc.) may be used. Triethyl citrate is an especially preferred plasticizer for the aqueous dispersions of ethyl cellulose of the present invention.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of ethyl cellulose of the present invention.

It has further been found that the addition of a small amount of talc reduces the tendency of the aqueous dispersion to stick during processing, and acts as a polishing agent.

One commercially-available aqueous dispersion of ethylcellulose is Aquacoat® (FMC Corp., Philadelphia, Pa., U.S.A.). Aquacoat® is prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, it is necessary to intimately mix the Aquacoat® with a suitable plasticizer prior to use.

Another aqueous dispersion of ethylcellulose is commercially available as Surelease® (Colorcon, Inc., West Point, Pa., U.S.A.). This product is prepared by incorporating plasticizer into the dispersion during the manufacturing process. A hot melt of a polymer, plasticizer (dibutyl sebacate), and stabilizer (oleic acid) is prepared as a homogeneous mixture, which is then diluted with an alkaline solution to obtain an aqueous dispersion which can be applied directly onto substrates.

In one preferred embodiment, the acrylic coating is an acrylic resin lacquers used in the form of an aqueous dispersion, such as that which is commercially available from Rohm Pharma under the Tradename Eudragit®. In further preferred embodiments, the acrylic coating comprises a mixture of two acrylic resin lacquers commercially available from Rohm Pharma under the Tradenames Eudragit® RL 30 D and Eudragit® RS 30 D, respectively. Eudragit® RL 30 D and Eudragit® RS 30 D are copolymers of acrylic and methacrylic esters with a low content of quaternary ammonium groups, the molar ratio of ammonium groups to the remaining neutral (meth)acrylic esters being 1:20 in Eudragit® RL 30 D and 1:40 in Eudragit® RS 30 D. The mean molecular weight is about 150,000. The code designations RL (high permeability) and RS (low permeability) refer to the permeability properties of these agents. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a controlled-release formulation having a desirable dissolution profile. Desirable controlled-release formulations may be obtained, for instance, from a retardant coating derived from 100% Eudragit® RL, 50% Eudragit® RL and 50% Eudragit® RS, and 10% Eudragit® R: Eudragit® 90% RS. Of course, one skilled in the art will recognize that other acrylic polymers may also be used, such as, for example, Eudragit® L.

In addition to modifying the dissolution profile by altering the relative amounts of different acrylic resin lacquers, the dissolution profile of the ultimate product may also be modified, for example, by increasing or decreasing the thickness of the retardant coating.

When the aqueous dispersion of hydrophobic polymer is used to coat inert pharmaceutical beads such as nu pariel 18/20 beads, a plurality of the resultant stabilized solid controlled-release beads may thereafter be placed in a gelatin capsule in an amount sufficient to provide an effective controlled-release dose when ingested and contacted by gastric fluid.

The stabilized controlled-release formulations of the present invention slowly release the therapeutically active agent, e.g. when ingested and exposed to gastric fluids, and then to intestinal fluids. The controlled-release profile of the formulations of the invention can be altered, for example, by varying the amount of overcoating with the aqueous dispersion of hydrophobic polymer, altering the manner in which the plasticizer is added to the aqueous dispersion of hydrophobic polymer, by varying the amount of plasticizer relative to hydrophobic polymer, by the inclusion of additional ingredients or excipients, by altering the method of manufacture, etc.

Spheroids or beads coated with a therapeutically active agent are prepared, e.g. by dissolving the therapeutically active agent in water and then spraying the solution onto a substrate, for example, nu pariel 18/20 beads, using a Wuster insert. Optionally, additional ingredients are also added prior to coating the heads in order to assist the hydromorphone binding to the beads, and/or to color the solution, etc. For example, a product which includes hydroxypropyl methylcellulose, etc. with or without colorant may be added to the solution and the solution mixed (e.g., for about 1 hour) prior to application of the same onto the beads. The resultant coated substrate, in this example beads, may then be optionally overcoated with a barrier agent, to separate the therapeutically active agent from the hydrophobic controlled-release coating. An example of a suitable barrier agent is one which comprises hydroxypropyl methylcellulose. However, any film-former known in the art may be used. It is preferred that the barrier agent does not affect the dissolution rate of the final product.

The hydromorphone, HPMC protected (optional) beads may then be overcoated with an aqueous dispersion of the hydrophobic polymer. The aqueous dispersion of hydrophobic polymer preferably further includes an effective amount of plasticizer, e.g. triethyl citrate. Pre-formulated aqueous dispersions of ethylcellulose, such as Aquacoat® or Surelease®, may be used. If Surelease® is used, it is not necessary to separately add a plasticizer. Alternatively, pre-formulated aqueous dispersions of acrylic polymers such as Eudragit® can be used.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the aqueous dispersion of hydrophobic polymer. For example, color be added to Aquacoat® via the use of alcohol or propylene glycol based color dispersions, milled aluminum lakes and opacifiers such as titanium dioxide by adding color with shear to water soluble polymer solution and then using low shear to the plasticized Aquacoat®. Alternatively, any suitable method of providing color to the formulations of the present invention may be used. Suitable ingredients for providing color to the formulation when an aqueous dispersion of an acrylic polymer is used include titanium dioxide and color pigments, such as iron oxide pigments. The incorporation of pigments, may, however, increase the retard effect of the coating.

The plasticized aqueous dispersion of hydrophobic polymer may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the aqueous dispersion of hydrophobic polymer to obtain a predetermined controlled-release of said therapeutically active agent when said coated substrate is exposed to aqueous solutions, e.g. gastric fluid, is preferably applied, taking into account the physical characteristics of the therapeutically active agent, the manner of incorporation of the plasticizer, etc. After coating with the hydrophobic polymer, a further overcoat of a film-former, such as Opadry®, is optionally applied to the beads. This overcoat is provided, if at all, in order to substantially reduce agglomeration of the beads.

Next, the coated beads are cured in order to obtain a stabilized release rate of the therapeutically active agent.

To date, attempts to prepare stable controlled-release pharmaceutical formulations using aqueous dispersions of hydrophobic polymers have been unsuccessful due to stability problems. In particular, when coating these pharmaceutical forms using aqueous polymeric dispersions to obtain a desired release profile of the active drug(s) over several hours or longer, it is known in the art that the dissolution release profile changes on ageing.

This problem has been overcome in the embodiment of the present invention wherein an aqueous dispersion of ethylcellulose is used as the controlled-release coating, wherein the curing step is accomplished by subjecting the coated substrate to a temperature greater, than the glass transition temperature of the coating solution (i.e., ethylcellulose) and at a relative humidity from about 60% to about 100%, until the curing endpoint is reached.

In preferred embodiments of the present invention, the stabilized product derived from an aqueous dispersion of ethylcellulose is obtained by subjecting the coated substrate to oven curing at elevated temperature/humidity levels for the required time period, the optimum values for temperature, humidity and time for the particular formulation being determined experimentally. In certain embodiments of the present invention, the stabilized product coated with an aqueous dispersion of ethylcellulose is obtained via an oven curing conducted at a temperature of about 60° C. and a relative humidity from about 60% to about 100% for a time period from about 48 to about 72 hours. This is the case for the hydromorphone beads described in the examples provided below. However, one skilled in the art will recognize that necessary curing conditions may be changed somewhat, and may in fact be broader than the above-mentioned temperature, humidity and time ranges, depending upon the particular formulation, in order to obtain a stabilized product.

Traditionally, curing has been carried out for Eudragit® coated formulations, if at all, via a fluid bed at 45° C. for 2 hours after application. Such a standard curing is recommended by Rohm Pharma because it is above the glass transition temperature (Tg) of Eudragit® RS 30 D plasticized with triethylcitrate at a 20% level of solids. This recommended curing does not stabilize the dissolution profile of the formulation upon storage, as will be demonstrated by the examples set forth herein.

This problem is overcome in the embodiment of the present invention wherein the aqueous dispersion of hydrophobic polymer comprises an aqueous dispersion of an acrylic polymer such as Eudragit®, wherein the stabilized product is obtained via an oven curing conducted at a temperature greater than the Tg of the coating formulation and continuing the curing until an endpoint is reached at which the coated formulation attains a dissolution profile which is substantially unaffected by exposure to storage conditions of elevated temperature and/or humidity. Generally, the curing time is, e.g., about 24 hours or more, and the curing temperature may be, for example, about 45° C. It has further been discovered that it is not necessary to subject the coated substrate to humidity levels above ambient conditions during the curing step in order to achieve a stabilized end product:

In preferred embodiments of the present invention directed to the acrylic coating, the stabilized product is obtained by subjecting the coated substrate to oven curing at a temperature above the Tg of the plasticized acrylic polymer for the required time period, the optimum values for temperature and time for the particular formulation being determined experimentally. In certain embodiments of the present invention, the stabilized product is obtained via an oven curing conducted at a temperature of about 45° C. for a time period from about 24 to about 48 hours. It is also contemplated that certain products coated with the controlled-release coating of the present invention may require a curing time longer than 24 hours, e.g., from about 24 to about 48 hours, or even 60 hours or more.

The release of the therapeutically active agent from the controlled-release formulation of the present invention can be further influenced, i.e., adjusted to a desired rate, by the addition of one or more release-modifying agents, or by providing one or more passageways through the coating. The ratio of hydrophobic polymer to water soluble material is determined by, among other factors, the release rate required and the solubility characteristics of the materials selected.

The release-modifying agents which function as pore-formers may be organic or inorganic, and include materials that can be dissolved, extracted or leached from the coating in the environment of use. The pore-formers may comprise one or more hydrophilic polymers such as hydroxypropylmethylcellulose.

The controlled-release coatings of the present invention can also include erosion-promoting agents such as starch and gums.

The controlled-release coatings of the present invention can also include materials useful for making microporous lamina in the environment of use, such as polycarbonates comprised of linear polyesters of carbonic acid in which carbonate groups reoccur in the polymer chain.

The release-modifying agent may also comprise a semipermeable polymer.

In certain preferred embodiments, the release-modifying agent is selected from hydroxypropylmethylcellulose, lactose, metal stearates, and mixtures of any of the foregoing.

The controlled-release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc.

In other embodiments of the present invention, the controlled-release formulation is achieved via a release matrix having a controlled-release coating as set forth above, the present invention may utilize a controlled-release matrix that affords in-vitro dissolution rates of the opioid within the narrow ranges required and that releases the opioid in a pH-independent manner. Suitable materials for inclusion in a controlled-release matrix are (a) Hydrophilic polymers, such as gums, cellulose ethers, acrylic resins and protein derived materials. Of these polymers, the cellulose ethers, especially hydroxyalkylcelluloses and carboxyalkylcelluloses, are preferred. The oral dosage form may contain between 1% and 80% (by weight) of at least one hydrophilic or hydrophobic polymer.

(b) Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes. Hydrocarbons having a melting point of between 25° and 90° C. are preferred. Of these long chain hydrocarbon materials, fatty (aliphatic) alcohols are preferred. The oral dosage form may contain up to 60% (by weight) of at least one digestible, long chain hydrocarbon.

(c) Polyalkylene glycols. The oral dosage form may contain up to 60% (by weight) of at least one polyalkylene glycol.

One particular suitable matrix comprises at least one water soluble hydroxyalkyl cellulose, at least one $C_{12}$-$C_{36}$, preferably $C_{14}$-$C_{22}$, aliphatic alcohol and, optionally, at least one polyalkylene glycol. The at least one hydroxyalkyl cellulose is preferably a hydroxy ($C_1$ to $C_6$) alkyl cellulose, such as hydroxypropylcellulose, hydroxypropylmethylcellulose and; especially, hydroxyethyl cellulose. The amount of the at least one hydroxyalkyl cellulose in the present oral dosage form will be determined, inter alia, by the precise rate of opioid release required. The at least one aliphatic alcohol may be, for example, lauryl alcohol, myristyl alcohol or stearyl alcohol. In particularly preferred embodiments of the present oral dosage form, however, the at least one aliphatic alcohol is cetyl alcohol or cetostearyl alcohol. The amount of the at least one aliphatic alcohol in the present oral dosage form will be determined, as above, by the precise rate of opioid release required. It will also depend on whether at least one polyalkylene glycol is present in or absent from the oral dosage form. In the absence of at least one polyalkylene glycol, the oral dosage form preferably contains between 20% and 50% (by wt) of the at least one aliphatic alcohol. When at least one polyalkylene glycol is present in the oral dosage form, then the combined weight of the at least one aliphatic alcohol and the at least one polyalkylene glycol preferably constitutes between 20% and 50% (by wt) of the total dosage.

In one embodiment, the ratio of, e.g., the at least one hydroxyalkyl cellulose or acrylic resin to the at least one aliphatic alcohol/polyalkylene glycol determines, to a considerable extent, the release rate of the opioid from the formulation. A ratio of the at least one hydroxyalkyl cellulose to the at least one aliphatic alcohol/polyalkylene glycol of between 1:2 and 1:4 is preferred, with a ratio of between 1:3 and 1:4 being particularly preferred.

The at least one polyalkylene glycol may be, for example, polypropylene glycol or, which is preferred, polyethylene glycol. The number average molecular weight of the at least one polyalkylene glycol is preferred between 1000 and 15000 especially between 1500 and 12000.

Another suitable controlled-release matrix would comprise an alkylcellulose (especially ethyl cellulose), a $C_{12}$ to $C_{36}$ aliphatic alcohol and, optionally, a polyalkylene glycol.

In addition to the above ingredients, a controlled-release matrix may also contain suitable quantities of other materials, e.g. diluents, lubricants, binders, granulating aids, colorants, flavorants and glidants that are conventional in the pharmaceutical art.

In order to facilitate the preparation of a solid, controlled release, oral dosage form according to this invention there is provided, in a further aspect of the present invention, a process for the preparation of a solid, controlled release, oral dosage form according to the present invention comprising incorporating opioids or a salt thereof in a controlled-release matrix. Incorporation in the matrix may be effected, for example, by (a) forming granules comprising at least one water soluble hydroxyalkyl cellulose and opioid or an opioid salt, (b) mixing the hydroxyalkyl cellulose containing granules with at least one $C_{12}$-$C_{36}$ aliphatic alcohol, and (c) optionally, compressing and shaping the granules. Preferably, the granules are formed by wet granulating the hydroxyalkyl cellulose/opioid with water. In a particularly preferred embodiment of this process, the amount of water added during the wet granulation step is preferably between 1.5 and 5 times, especially between 1.75 and 3.5 times, the dry weight of the opioid.

In yet other alternative embodiments, a spheronizing agent, together with the active ingredient can be spheronized to form spheroids. Microcrystalline cellulose is preferred. A suitable microcrystalline cellulose is, for example, the material sold as Avicel PH 101™ (FMC Corporation). In such embodiments, in addition to the active ingredient and spheronizing agent, the spheroids may also contain a binder. Suitable binders, such as low viscosity, water soluble polymers, will be well known to those skilled in the pharmaceutical art. However, water soluble hydroxy lower alkyl cellulose, such as hydroxy propyl cellulose, are preferred. Additionally (or alternatively) the spheroids may contain a water insoluble polymer, especially an acrylic polymer, an acrylic copolymer, such as a methacrylic acid-ethyl acrylate copolymer, or ethyl cellulose. In such embodiments, the controlled-release coating will generally include a water insoluble material such as (a) a wax, either alone or in admixture with a fatty alcohol; or (b) shellac or zein.

DETAILED DESCRIPTION OF THE PREFERRED EMBODIMENTS

The following examples illustrate various aspects of the present invention. They are not meant to be construed to limit the claims in any manner whatsoever.

EXAMPLE 1

Controlled Release Hydromorphone

HCl 8 mg Formulations

Acrylic Polymer Coating

Example 1 was prepared as follows:

1. Drug Loading. Hydromorphone beads were prepared by dissolving hydromorphone HCl in water, adding Opadry Y-5-1442, light pink (a product commercially available from Colorcon, West Point, Pa., which contains hydroxypropyl methylcellulose, hydroxypropyl cellulose, titanium dioxide, polyethylene glycol and D&C Red No. 30 aluminum lake) and mixing for about 1 hour to obtain a 20% w/w suspension. This suspension was then sprayed onto Nu-Pareil 18/20 mesh beads using a Wurster insert.

2. First Overcoat. The loaded hydromorphone beads were then overcoated with a 5% w/w gain of Opadry Light Pink using a Wurster insert. This overcoat was applied as a protective coating.

3. Retardant Coat. After the first overcoat, the hydromorphone beads were then coated with a 5% weight gain of a retardant coating mixture of Eudragit RS 30D and Eudragit RL 30D at a ratio of 90:10, RS to RL. The addition of Triethyl Citrate (a plasticizer) and Talc (anti-tacking agent) was also included in the Eudragit suspension. The Wurster insert was used to apply the coating suspension.

4. Second Overcoat. Once the retardant coating was complete, the hydromorphone beads were given a final overcoat of Opadry Light Pink to a 5% weight gain using a Wurster insert. This overcoat was also applied as a protective coating.

5. Curing. After the completion of the final overcoat, the hydromorphone beads were cured in a 45° C. oven for 2 days. The cured beads were then filled into gelatin capsules at an 8 mg Hydromorphone strength. The complete formula for the beads of Example 1 is set forth in Table 1 below:

TABLE I

| Processing Step | Ingredient | $ | mg/unit |
| --- | --- | --- | --- |
| Drug Loading | Hydromorphone HCl | 8.2 | 8.0 |
| | Nu-Pareil 18/20 | 73.3 | 74.0 |
| | Opadry Lt Pink | 2.1 | 2.0 |
| First Overcoat | Opadry Lt Pink 4.4 | 4.2 | |

TABLE I-continued

| Processing Step | Ingredient | % | mg/unit |
|---|---|---|---|
| Retardant Coat | Eudragit RS 30D (dry wt.) | 4.0 | 3.8 |
| | Eudragit RL 30D (dry wt.) | 0.4 | 0.4 |
| | Triethyl Citrate | 0.8 | 0.8 |
| | Talc | 1.8 | 1.7 |
| Second Overcoat | Opadry Lt Pink | 5.0 | 4.8 |
| Total | | 100.0 | 99.7 mg |

Dissolution studies were conducted on the Eudragit-coated hydromorphone beads of Example 1 both initially and after 28 days. The results are set forth in Table 2 below:

TABLE 2

| | Time | | | | | | |
|---|---|---|---|---|---|---|---|
| | 1 hr | 2 hr | 4 hr | 8 hr | 12 hr | 18 hr | 24 hr |
| Initial | 17.2 | 48.4 | 77.4 | 93.3 | 97.2 | 98.8 | 98.8 |
| 28 days | 16.8 | 50.6 | 79.7 | 95.2 | 99.0 | 101.9 | 102.7 |

The stability studies of the Eudragit-coated hydromorphone beads as set forth in Table 2 below show the initial dissolution to be the same as the dissolution done on samples placed at a 37° C./80% RH condition.

EXAMPLES 2-4

Controlled Release Hydromorphone

HCl 8 mg Formulations

Ethylcellulose Coatings

Examples 2-4 were prepared as follows:

1. Drug Loading. Hydromorphone beads were prepared by dissolving hydromorphone HCl in water, adding Opadry Y-5-1442, light pink (a product commercially available from Colorcon, West Point, Pa., which contains hydroxypropyl methylcellulose, hydroxypropyl cellulose, titanium dioxide, polyethylene glycol and D&C Red No. 30 aluminum lake) and mixing for about 1 hour to obtain a 20% w/w suspension. This suspension was then sprayed onto Nu-Pareil 18/20 mesh beads using a Wurster insert.

2. First Overcoat. The loaded hydromorphone beads were then overcoated with a 5% w/w gain of Opadry Light Pink using a Wurster insert. This overcoat was applied as a protective coating and provides immediate release hydromorphone beads. See Table 3 below:

TABLE 3

| | Immediate Release Beads | | |
|---|---|---|---|
| Processing Step | Ingredient | % | mg per Unit |
| Drug Loading | Hydromorphone HCl | 8.7 | 8.0 |
| | Nu-Pareil 18/20 | 83.9 | 74.0 |
| | Opadry Lt Pink | 2.4 | 2.0 |
| First Overcoat | Opadry Lt Pink | 5.0 | 4.2 |
| Total | | 100.0 | 88.2 mg |

3. Retardant Coat. After the first overcoat, the hydromorphone beads were than coated with a retardant coating of Aquacoat ECD 30 and Triethyl Citrate (a plasticizer) to a 5%, 10% and 15% (Example 4) weight gain (based on dry wt. of Aquacoat). A Wurster insert was used to apply the coating suspensions.

4. Curing. After the application of the retardant coating, the beads were placed in a 60° C. oven containing a tray of water to maintain about a 85% relative humidity level. All three batches were allowed to cure for 72 hours.

5. Second Overcoat. The cured beads were removed from the humid oven, and dried in a fluid bed dryer for about one hour. The dried cured beads were then overcoated with a 5% w/w gain of Opadry Light Pink using a Wurster insert. This overcoat was applied as a protective coating. The final formulations for beads having 5%, 10%, and 15% Aquacoat coatings are set forth in Tables 4, 5 and 6 below, respectively:

TABLE 4

| | Beads with 5% Aquacoat Coating | | |
|---|---|---|---|
| Processing Step | Ingredient | % | mg per Unit |
| Drug Loading | Hydromorphone HCl | 8.2 | 8.0 |
| | Nu-Pareil 18/20 | 74.8 | 74.0 |
| | Opadry Lt Pink | 2.1 | 2.0 |
| First Overcoat | Opadry Lt Pink | 4.5 | 4.2 |
| Retardant Coat | Aquacoat ECD 30 (dry wt.) | 4.5 | 4.2 |
| | Triethyl Citrate | 0.9 | 0.8 |
| Second Overcoat | Opadry Lt Pink | 5.0 | 4.7 |
| Total | | 100.0 | 97.9 mg |

TABLE 5

| | Beads with 10% Aquacoat Coating | | |
|---|---|---|---|
| Processing Step | Ingredient | % | mg per Unit |
| Drug Loading | Hydromorphone HCl | 8.0 | 8.0 |
| | Nu-Pareil 18/20 | 70.5 | 74.0 |
| | Opadry Lt Pink | 2.0 | 2.0 |
| First Overcoat | Opadry Lt Pink | 4.2 | 4.2 |
| Retardant Coat | Aquacoat ECD 30 (dry wt.) | 8.5 | 8.4 |
| | Triethyl Citrate | 1.7 | 1.7 |
| Second Overcoat | Opadry Lt Pink | 5.1 | 5.0 |
| Total | | 100.0 | 103.3 mg |

TABLE 6

| | Beads with 15% Aquacoat Coating | | |
|---|---|---|---|
| Processing Step | Ingredient | % | mg per Unit |
| Drug Loading | Hydromorphone HCl | 7.8 | 8.0 |
| | Nu-Pareil 18/20 | 66.8 | 74.0 |
| | Opadry Lt Pink | 1.9 | 2.0 |
| First Overcoat | Opadry Lt Pink | 4.0 | 4.2 |
| Retardant Coat | Aquacoat ECD 30 (dry wt.) | 12.1 | 12.6 |
| | Triethyl Citrate | 2.4 | 2.5 |
| Second Overcoat | Opadry Lt Pink | 5.0 | 5.2 |
| Total | | 100.0 | 108.5 mg |

7. Encapsulation. The hydromorphone beads were then filled into hard gelatin capsules to a total of 8 mg hydromorphone HCl per capsule using the following combinations:

Example 2: All beads have 5% Aquacoat coating;
Example 3: 75% beads having 10% Aquacoat coating and 25% immediate release beads;
Example 4: 75% beads having 15% Aquacoat coating and 25% immediate release beads.

Dissolution studies were conducted on the Aquacoat-coated hydromorphone heads of Examples 2-4 both initially and after 28 days. The results are set forth in Tables 7-9 below:

TABLE 10

Dissolution of Example 2

| | Time | | | | | |
|---|---|---|---|---|---|---|
| 1 hr | 2 hr | 4 hr | 8 hr | 12 hr | 18 hr | 24 hr |
| Initial 33.8 | 54.6 | 71.2 | 85.7 | 92.9 | 97.3 | 99.9 |
| 28 days 34.0 | 53.1 | 70.8 | 86.1 | 93.1 | 98.2 | 100.7 |

TABLE 11

Dissolution of Example 3

| | Time | | | | | |
|---|---|---|---|---|---|---|
| 1 hr | 2 hr | 4 hr | 8 hr | 12 hr | 18 hr | 24 hr |
| Initial 31.6 | 43.4 | 59.2 | 72.3 | 79.2 | 85.7 | 90.3 |
| 28 days 32.3 | 43.7 | 59.2 | 72.6 | 80.7 | 86.8 | 91.5 |

TABLE 12

Dissolution of Example 4

| | Time | | | | | |
|---|---|---|---|---|---|---|
| 1 hr | 2 hr | 4 hr | 8 hr | 12 hr | 18 hr | 24 hr |
| Initial 29.3 | 37.2 | 52.1 | 66.4 | 73.9 | 80.4 | 85.4 |
| 28 days 31.1 | 37.0 | 51.4 | 66.0 | 73.7 | 81.3 | 86.2 |

Stability studies of the Aquacoat-coated hydromorphone beads of Examples 2-4, as set forth above, show the initial dissolutions to be the same as dissolutions done on samples placed at 37° C./80% RH conditions.

EXAMPLES 5-8

In Examples 5-8, a single dose six-way randomized crossover study (one week wash-out) was conducted in 12 patients and compared to the results obtained with an equivalent close of an immediate release preparation. Blood samples were taken initially, 0.25, 0.5, 0.75, 1, 1.5, 2, 2.5, 3, 3.5, 4, 6, 8, 10, 12, 18, 24, 30, 36 and 48 hours after administration in order to determine plasma levels. Comparative Example A is 8 mg of a hydromorphone immediate release formulation (two tablets of Dilaudid® 4 mg tablets, commercially available from Knoll). Example 5 is an 8 mg dose of the encapsulated hydromorphone beads of Example 1. Example 6 is an 8 mg dose of the encapsulated hydromorphone beads of Example 2. Example 7 is an 8 mg dose of the encapsulated hydromorphone beads of Example 3. Example 8 is an 8 mg dose of the encapsulated hydromorphone beads of Example 4.

Figure 2:
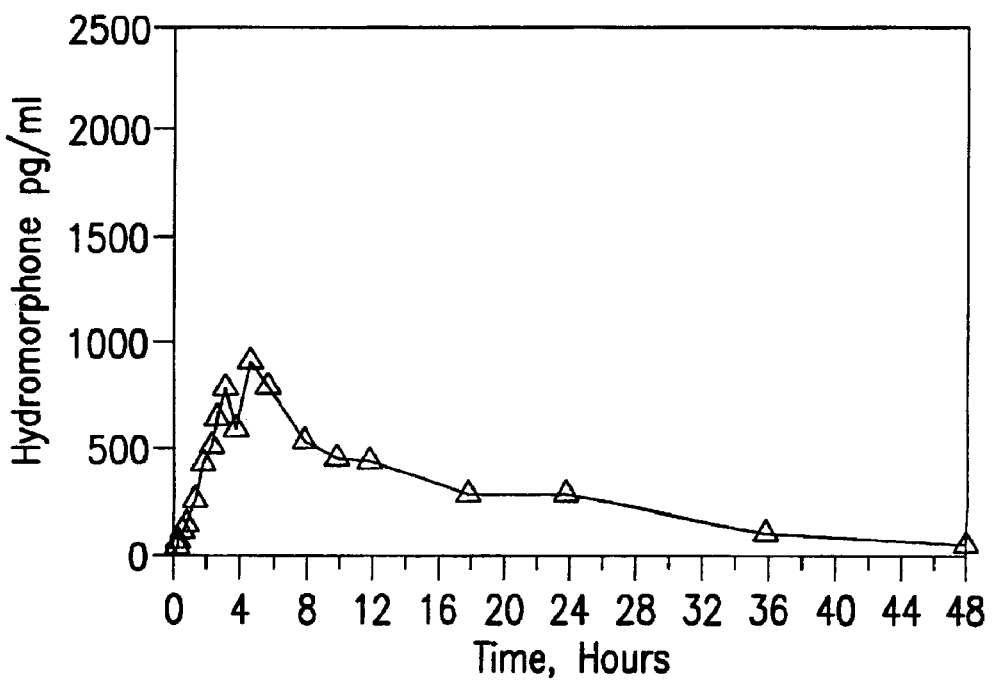
FIG. 2 is a graphical representation of the plasma levels obtained for Example 5.
Figure 3:
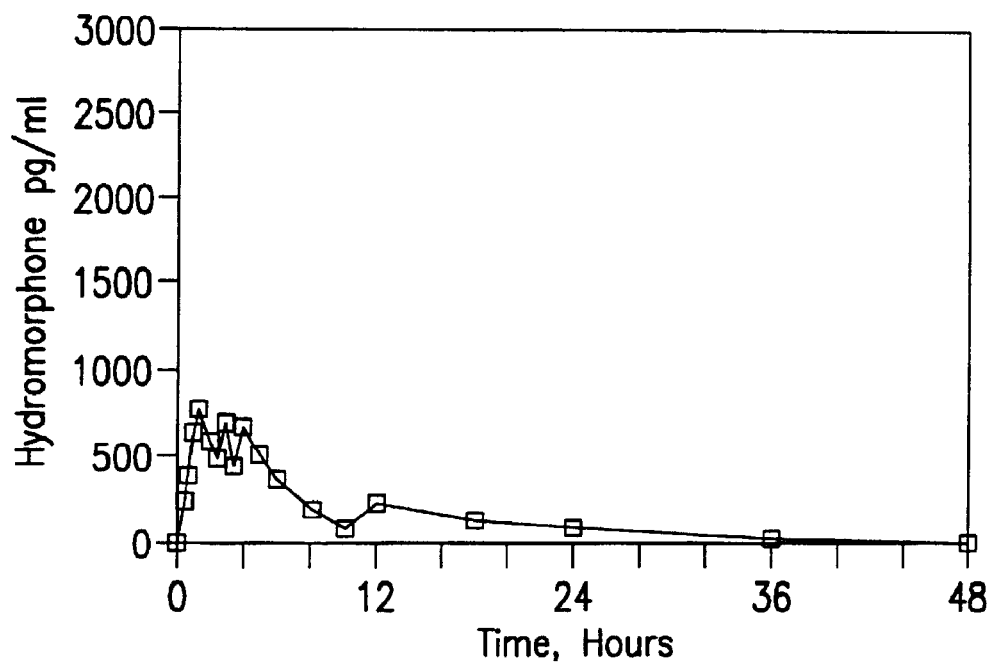
FIG. 3 is a graphical representation of the plasma levels obtained for Example 6.
Figure 4:
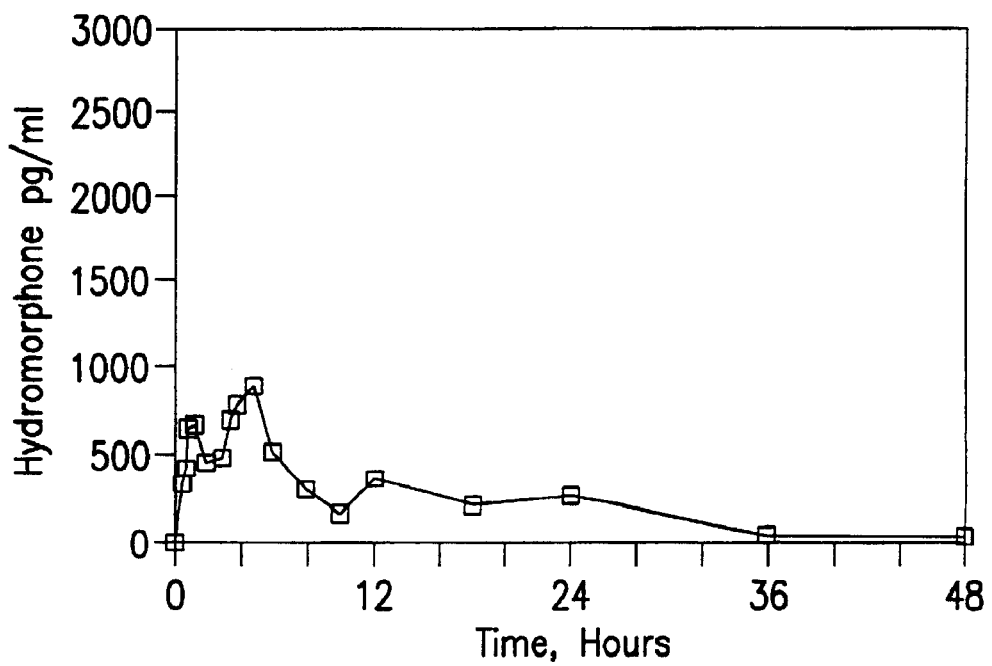
FIG. 4 is a graphical representation of the plasma levels obtained for Example 7.
Figure 5:
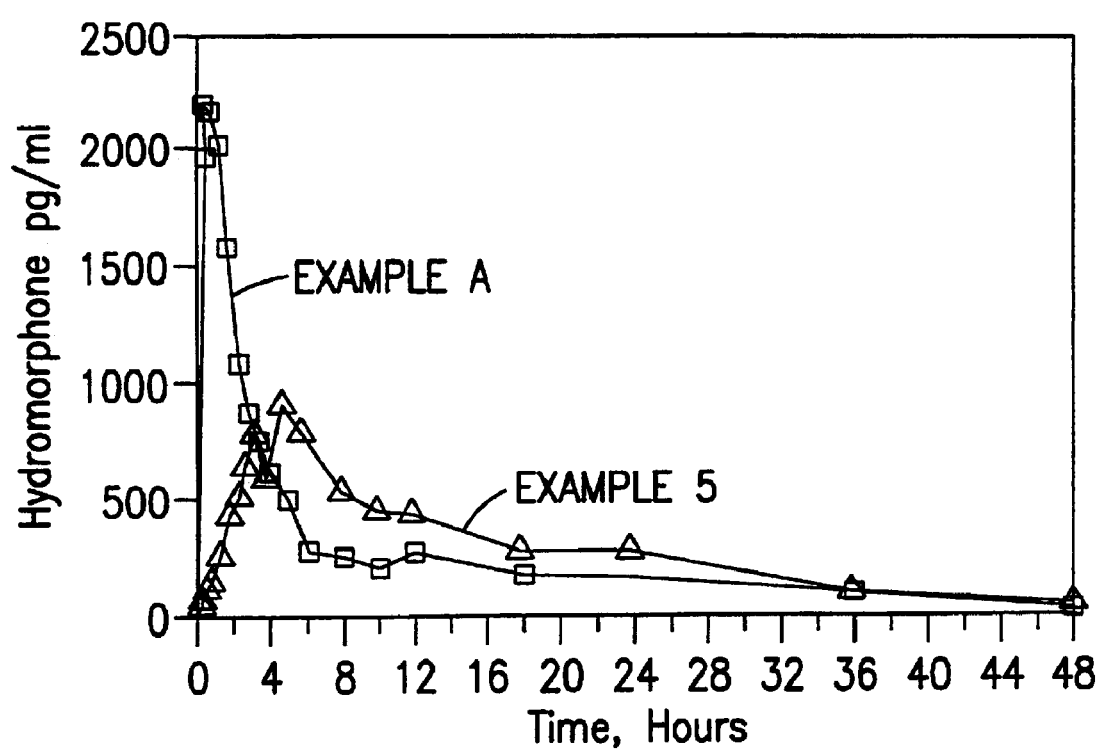
FIG. 5 is a graphical representation of the plasma levels obtained for Example 5 plotted against the results obtained for Comparative Example A.

The results obtained for Comparative Example A are set forth in FIG. 1. The results obtained for Example 5 are set forth in FIG. 2. The results obtained for Example 6 are set forth in FIG. 3. The results obtained for Example 7 are set forth in FIG. 4. FIG. 5 shows the plasma levels of Example 5 plotted against the results for Comparative Example A. The results for Examples 5-8 are further set forth in Tables 13 and 14 below, which provide data regarding area under the curve (bioavailability), the peak plasma concentration ($C_{max}$), and the time to reach peak plasma concentration ($t_{max}$).

TABLE 13

| Product | AUC | Cmax | Tmax |
|---|---|---|---|
| Comparative Example 1 | | | |
| 2 Dilaudid Tablets | 12427 | 3013 | 1.10 |
| Example 6 | 6718 | 1070 | 2.58 |
| Example 7 | 9933 | 1265 | 2.39 |
| Example 8 | 8695 | 1138 | 0.88 |

TABLE 14

| Product | AUC | Cmax | Tmax | PW@IIII |
|---|---|---|---|---|
| 2 Dilaudid 4 mg Tablets | 12427 ± 1792 | 3013 ± 539 | 1.10 ± 0.14 | 1.67 ± 0.22 |
| Example 5 | 13707 ± 1381 | 1211 ± 153 | 4.42 ± 0.38 | 7.79 ± 1.96 |
| Example 5 | 110% | 40% | 402% | 466% |

It may be concluded with respect to Example 7 that it is 88% bioavailable (which is acceptable to regulatory agencies such as the U.S. FDA); Example 7 has a reduced $C_{max}$ of about one-half that of the Comparative Example A; and has a $t_{max}$ of 2.39 hours, as compared to a $t_{max}$ of 1.1 hours for Comparative Example A.

Dilaudid is known to be effective for about 6 hours. As can be ascertained from FIG. 1, blood levels for 8 mg Dilaudid at 6 hours were about 300 pg/ml hydromorphone. Therefore, a circulating concentration of about 300 pg/ml should be an effective analgesic concentration in the plasma.

In contrast, the results obtained for Example 5 showed that at the 12th hour after administration, the blood levels of hydromorphone were over 500 pg/ml hydromorphone, and at the 24th hour after administration, the plasma levels were well over 300 pg/ml. Therefore, this product is considered to be suitable for once a day administration, and is considered to be an opioid-sparing formulation.

Example 7, on the other hand, provided levels of over 300 pg/ml at the 12th hour after administration, with levels of about 250 pg/ml at the 24th hour after administration. However, the dose of hydromorphone administered in Example 7 was only 8 mg every 24 hours. In contrast, in order to maintain analgesia using the immediate-release formulation, the total dose necessary over the same period would be 16 mg (4 mg every 6 hours). From FIG. 4, it is apparent that if 2 capsules of Example 7 are administered, the minimum or trough concentration will be above the level of 300 pg/ml for the full 24 hour period. Two capsules of Example 7 would amount to the same dose over the 24 hour period as the immediate-release formulation. However, the amount of beads included in the final formulation might be adjusted to provide a final formulation having a 24 hour dose which is substantially less than the immediate-release formulation over the same period. Example 7 is therefore also considered to be an opioid sparing formulation. Therefore, this product is considered to be suitable for once a day administration.

EXAMPLES 9-10

In Examples 9-10, a single dose 4-way randomized crossover study was conducted in 10 subjects. Example 9 was an 8 mg dose of the hydromorphone beads of Example 5—fasted; whereas Example 10 is an 8 mg dose of the hydromorphone beads of Example 5—fed. In Comparative Example B, 8 mg of immediate release hydromorphone (2 Dilaudid 4 mg tablets) were administered—fasted. In Comparative Example C, 8 mg of immediate release hydromorphone (2 Dilaudid 4 mg tablets) were administered—fed.

Figure 6:
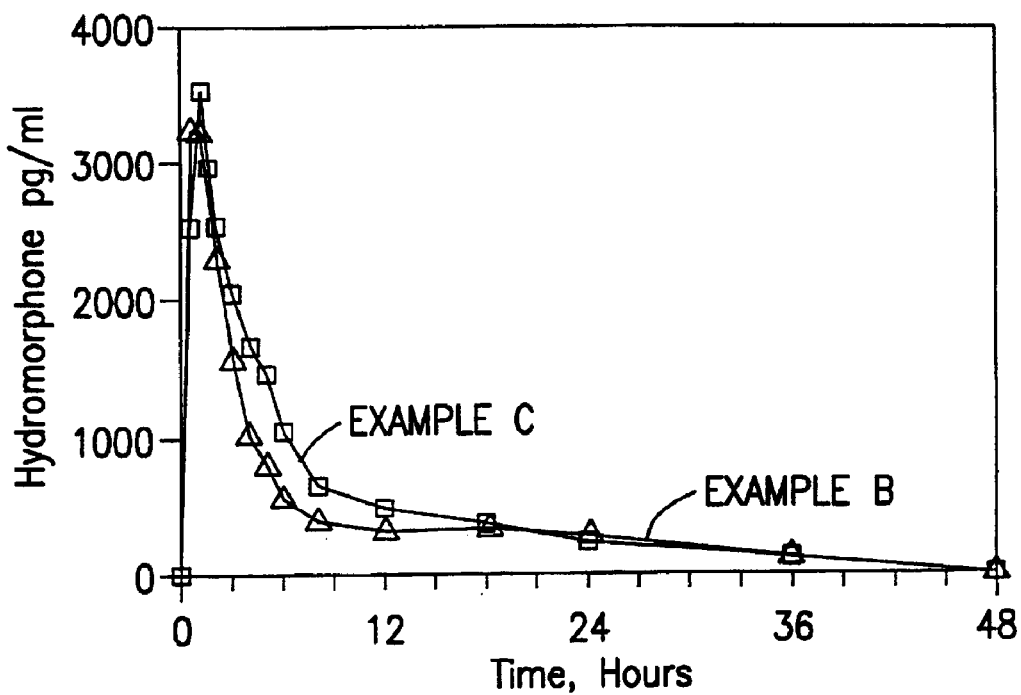
FIG. 6 is a graphical representation of the plasma levels obtained for Comparative Examples B and C.
Figure 7:
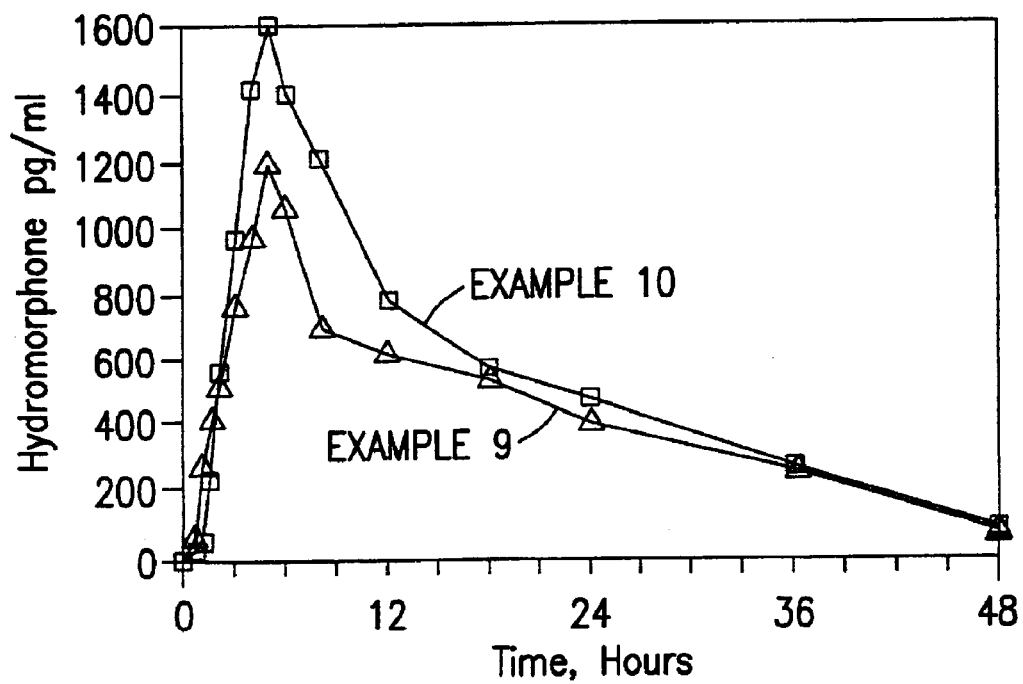
FIG. 7 is a graphical representation of the plasma levels obtained for Examples 9 and 10.

The plasma levels for Comparative Examples B and C are set forth in FIG. 6, whereas the plasma levels for Examples 9 and 10 are set forth in FIG. 7. The results for Examples 9-10 and Comparative Examples B and C are further set forth in Table 15, which provides data regarding area under the curve and percent absorbed as compared to immediate release (bioavailability), the peak plasma concentration ($C_{max}$), and the time to reach peak plasma concentration ($t_{max}$).

TABLE 15

| Group | AUC | % IR | $T_{max}$ | $C_{max}$ |
|---|---|---|---|---|
| Example 9 | 21059 | 101 | 4.9 | 1259 |
| Example 10 | 25833 | 106 | 4.6 | 1721 |
| Comparative Example B | 20903 | 100 | 0.85 | 3816 |
| Comparative Example C | 24460 | 100 | 1.15 | 3766 |

As can be ascertained from the results provided by Examples 9-10 and Comparative Examples B and C, there was a minimal food effect for both the immediate release tablets and the controlled-release beads of Examples 9 and 10, with a small increase in bioavailability for the controlled-release beads of Examples 9 and 10. The plasma levels again confirm that this product is suitable for once a day and twice a day administration. In the 24th hour, the controlled-release product provided plasma levels of nearly 600 pg/ml and at the 12th hour provided plasma levels of over 700 pg/ml.

EXAMPLES 11-12

In Examples 11-12, a steady state 3-way cross-over study was conducted for 4 days. In Comparative Example D, the subjects were dosed with 8 mg immediate release hydromorphone (2 Dilaudid 4 mg tablets) every 6 hours. In Example 11, 8 mg of the hydromorphone beads of Example 5 were administered every 12 hours. In Example 12, 8 mg of the hydromorphone beads of Example 5 were administered every 24 hours. On the fourth day, blood samples were taken.

Figure 8:
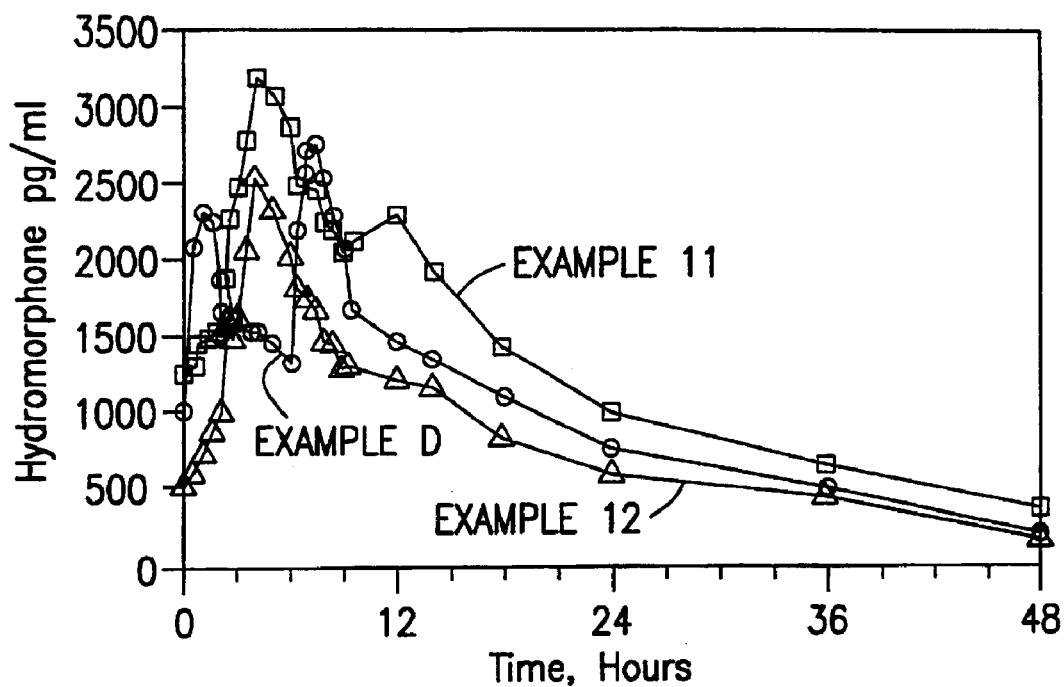
FIG. 8 is a graphical representation of the plasma levels obtained for Examples 11 and 12 plotted against the results obtained for Comparative Example D.
Figure 9:
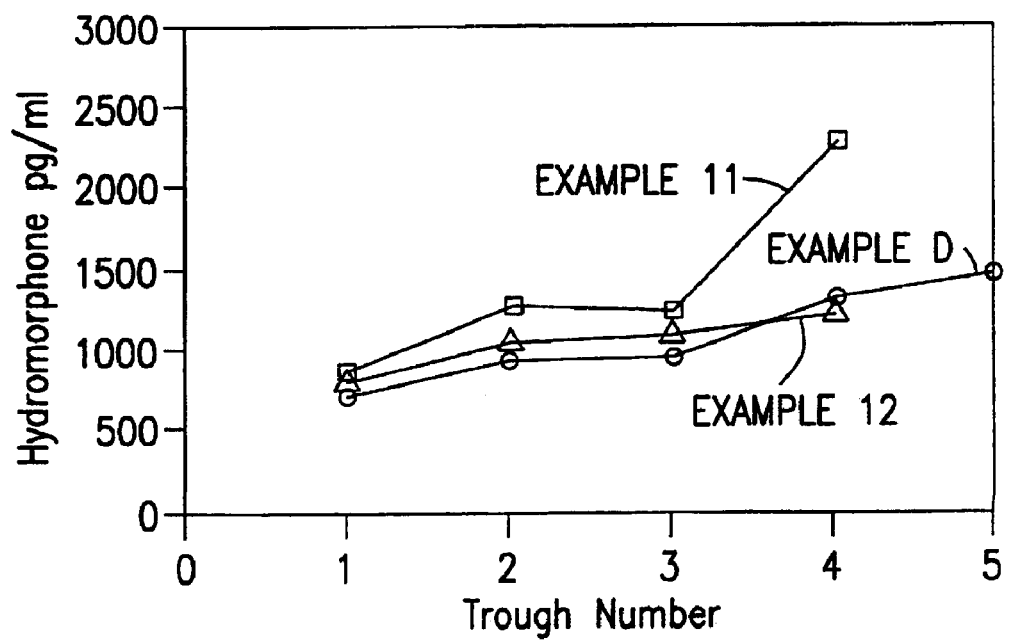
FIG. 9 As a graphical representation of the plasma levels obtained for Examples 11 and 12.

The plasma levels for Comparative Example D versus the plasma levels for Examples 11 and 12 are set forth in FIG. 8. The trough levels for Comparative Example D versus the plasma levels for Examples 11 and 12 are set forth in FIG. 9 (the values for Example 12 are doubled in FIG. 9. The results for Examples 11-12 and Comparative Example D are further set forth in Table 16, which provides data regarding area under the curve and percent absorbed as compared to immediate release (bioavailability), the peak plasma concentration ($C_{max}$), and the time to reach peak plasma concentration ($t_{max}$).

TABLE 16

| Group | AUC | AUC* | $T_{max}$ | $C_{max}$ | $C_{max}$* |
|---|---|---|---|---|---|
| Example 11 | 62223 | 27595 | 5.5 | 3475 | 2232 |
| Example 12 | 39233 | 28879 | 4.8 | 2730 | 2189 |
| Comparative Example D | 47835 | 22236 | 1.0 | 3124 | 2163 |

*AUC* = 12 hr. for Q12H, 0-24 hr. for Q24H, and 0-12 hr. for Q6H
*$C_{max}$* = $C_{max}$ minus zero time value With reference to the area under the curve (AUC) as a measure of bioavailability, it can be ascertained from the data provided in Table 16 that Comparative Example D and Examples 11 and 12 all have an equivalent AUC increased over the dosing interval, indicating that all dosage regimes are bioavailable.

Furthermore, in this study, Example 12 which was only dosed at 8 mg every 24 hours, shows that this formulation provides an excellent 24 hour preparation if the amount of beads are doubled to provide a once a day dosage of 16 mg, which is the equivalent amount of hydromorphone dosed by the immediate release formulation (4 mg every 6 hours). The minimum or trough concentration shown in FIG. 9 for Example 12 show that this product will be the equivalent of the 4 mg immediate release formulation (dosed every 6 hours), and therefore this would provide an excellent once a day product.

EXAMPLE 13

Controlled-Release Morphine Sulfate 30 mg Formulation

Acrylic Polymer Coating

Example 13 was prepared in the same manner as Example 1. The complete formula for the beads of Example 13 is set forth in Table 17 below:

TABLE 17

| Ingredients | Amt/Unit |
|---|---|
| Drug Loading | |
| Morphine Sulfate Powder | 30.0 mg |
| Lactose Hydrous Impalpable | 42.5 mg |
| Povidone | 2.5 mg |
| Nupareil PG 18/20 | 125.0 mg |
| Purified Water | qs |
| Opadry Red YS-1-1841 | 10.5 mg |
| Purified Water | qs |
| Retardant Coating | |
| Eudragit RS30D | 10.3 mg |
| Eudragit RL30D | 0.2 mg |
| Triethyl Citrate | 2.1 mg |
| Talc | 4.2 mg |
| Purified Water | qs |
| Second Overcoat | |
| Opadry Red YS-1-1841 | 12.0 |
| Purified Water | qs |
| Total | 239.3 mg |

The ratio of Eudragit RS30D to Eudragit RL30D is 98:2. After completion of the final overcoat, the morphine beads were cured in a 45° C. oven for 2 days. The cured heads were then filled into gelatin capsules at a 30 my strength.

Dissolution studies were conducted on the Eudragit-coated morphine beads of Example 13 both initially and after 3 months under accelerated storage conditions. The results are set forth in Table 18 below:

TABLE 18

| Storage Conditions Testing Time | Dissolution (% Dissoved) Time (Hr) | | | | |
|---|---|---|---|---|---|
| | 1 hr. | 2 Hrs. | 4 Hrs. | 8 Hrs. | 12 Hrs. |
| Initial | 2.6 | 24.7 | 60.5 | 89.4 | 98.8 |
| 1 Month 40° C./ 75% RH | 5.8 | 27.3 | 62.0 | 89.8 | 99.1 |
| 3 Months 40° C./ 75% RH | 6.8 | 26.5 | 65.3 | 87.6 | 95.1 |

The dissolutions set forth in Table 18 show the beads of Example 13 to be stable.

Figure 10:
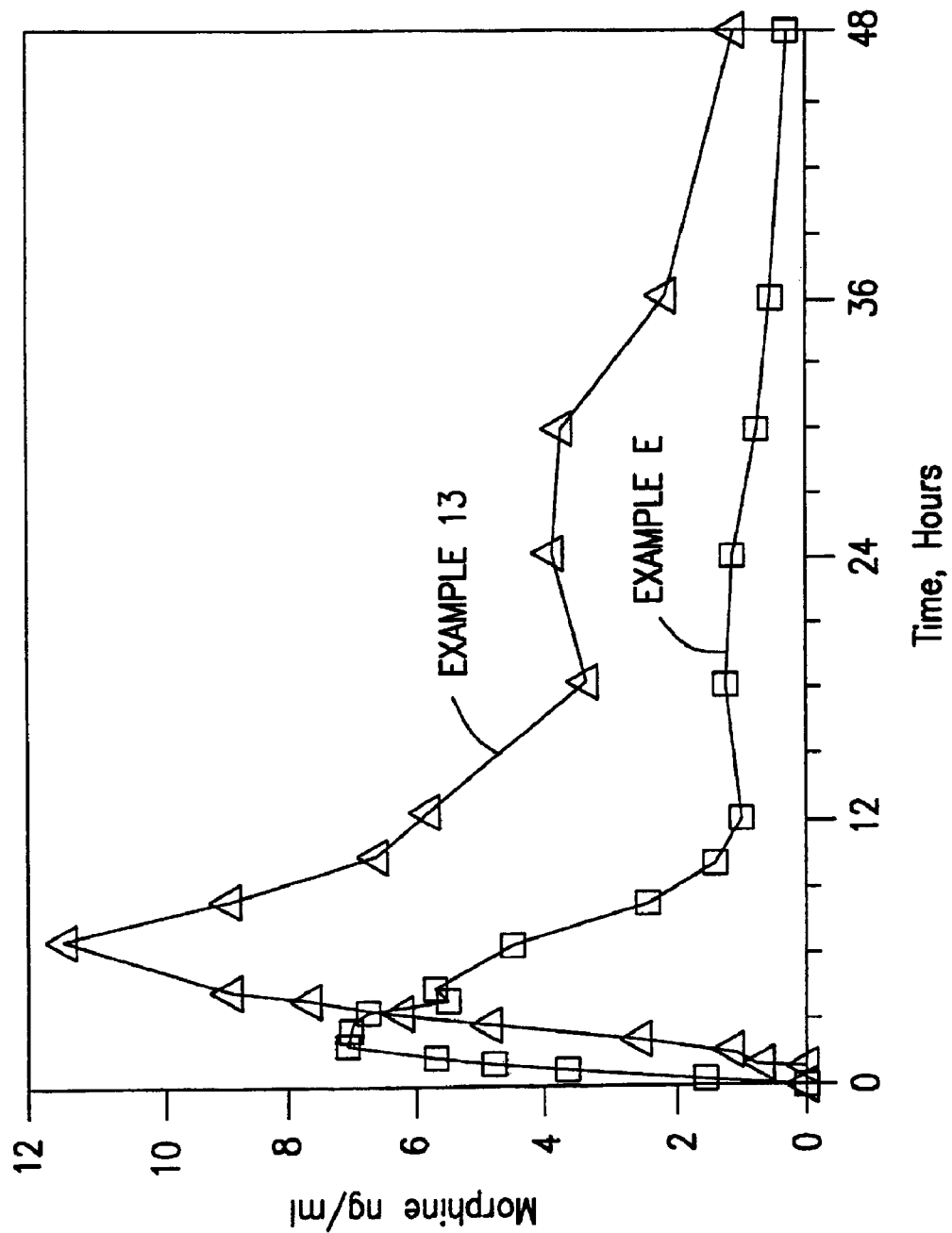
FIG. 10 is a graphical representation of the plasma levels obtained for Example 13 plotted against the plasma levels obtained for Comparative Example E.

A double-blind single dose cross-over study was then conducted in 12 subjects with regard to the dosage form of Example 13 against a standard formulation (Comparative Example E). In Comparative Example E, a commercially available controlled-release morphine sulfate tablet (MS Contin®, available from the Purdue Frederick Company) is administered. The results are set forth in FIG. 10, wherein the plasma levels of two times the dose of Example 13 are plotted against the plasma levels obtained with Comparative Example E.

The examples provided above are not meant to be exclusive. Many other variations of the present invention would be obvious to those skilled in the art, and are contemplated to be within the scope of the appended claims.

We claim:

1. A method for treating pain in humans for a time period of about 24 hours, comprising administering to a human patient at a dosing interval of about 24 hours a solid, controlled-release oral dosage form comprising 8 to 64 mg of hydromorphone or a pharmaceutically acceptable salt thereof incorporated into a controlled-release formulation comprising a tablet overcoated with a controlled-release coating derived from an aqueous dispersion of a hydrophobic polymer selected from the group consisting of a cellulosic polymer, an acrylic polymer, and mixtures thereof, wherein the coating has been stabilized by curing for about 24 hours or more at a temperature greater than the glass transition temperature of the hydrophobic polymer and a relative humidity from about 60% to about 100% such that the dosage form attains a dissolution profile which is substantially unaffected by exposure to storage conditions of at least one month at a temperature of 40° C. and a relative humidity of 75%, wherein (i) the dissolution rate in vitro of the dosage form, when measured by the USP Paddle Method of U.S. Pharmacopeia XXII (1990) at 100 rpm at 900 ml aqueous buffer at pH 1.6 and 7.2 and at 37° C., is such that from 12.5% to 42.5% (by wt) hydromorphone is released after 1 hour, from 25% to 65% (by wt) hydromorphone is released after 2 hours, from 45% to 85% (by wt) hydromorphone is released after 4 hours and greater than 60% (by wt) hydromorphone is released after 8 hours, and (ii) the in-vitro release rate is substantially independent of pH in that a difference, at any given time, between an amount of hydromorphone released at one pH and an amount released at any other pH, when measured in-vitro using the USP Paddle Method of U.S. Pharmacopeia XXII (1990) at 100 rpm in 900 ml aqueous buffer is no greater than 10%, the dosage form providing a duration of therapeutic effect of at least 24 hours and a mean $C_{max}$ of hydromorphone from about 1070 pg/ml to about 1721 pg/ml and a $T_{max}$ of between 4.6 and 8 hours, based on a single dose administration of the dosage form comprising 8 mg of hydromorphone hydrochloride.

2. The method of claim 1, wherein said dosage form comprises a pharmaceutically acceptable salt of hydromorphone.

3. The method of claim 1, wherein said dosage form comprises hydromorphone hydrochloride.

4. The method of claim 1, wherein the controlled release formulation further comprises a polymer selected from the group consisting of a pharmaceutically acceptable gum, an alkylcellulose, a cellulose ether, an acrylic resin, and mixtures of the foregoing.

5. The method of claim 4, wherein the controlled release formulation further comprises a digestible substituted or unsubstituted $C_8$-$C_{50}$ hydrocarbon.

6. The method of claim 5, wherein said hydrocarbon is selected from the group consisting of fatty acids, fatty alcohols, mineral oils, vegetable oils, waxes and mixtures of any of the foregoing.

7. The method of claim 4, wherein said dosage form further comprises a polyalkyleneglycol.

8. A method for treating pain in humans for a time period of about 24 hours, comprising administering to a human patient at a dosing interval of about 24 hours a solid, controlled-release oral dosage form comprising an active agent consisting essentially of 8 to 64 mg of hydromorphone or a pharmaceutically acceptable salt thereof incorporated into a controlled-release formulation comprising a tablet overcoated with a controlled-release coating derived from an aqueous dispersion of a hydrophobic polymer selected from the group consisting of a cellulosic polymer, an acrylic polymer, and mixtures thereof, wherein the coating has been stabilized by curing for about 24 hours or more at a temperature greater than the glass transition temperature of the hydrophobic polymer and a relative humidity from about 60% to about 100% such that the dosage form attains a dissolution profile which is substantially unaffected by exposure to storage conditions of at least one month at a temperature of 40° C. and a relative humidity of 75%, wherein (i) the dissolution rate in vitro of the dosage form, when measured by the USP Paddle Method of U.S. Pharmacopeia XXII (1990) at 100 rpm at 900 ml aqueous buffer at pH 1.6 and 7.2 and at 37° C., is such that from 12.5% to 42.5% (by wt) hydromorphone is released after 1 hour, from 25% to 65% (by wt) hydromorphone is released after 2 hours, from 45% to 85% (by wt) hydromorphone is released after 4 hours and greater than 60% (by wt) hydromorphone is released after 8 hours, and (ii) the in-vitro release rate is substantially independent of pH in that a difference, at any given time, between an amount of hydromorphone released at one pH and an amount released at any other pH, when measured in-vitro using the USP Paddle Method of U.S. Pharmacopeia XXII (1990) at 100 rpm in 900 ml aqueous buffer is no greater than 10%, the dosage form providing a duration of therapeutic effect of at least 24 hours, a mean $C_{max}$ of hydromorphone from about 1070 pg/ml to about 1721 pg/ml and a $T_{max}$ of between 4.6 to 8 hours, based on a single dose administration of the dosage form comprising 8 mg of hydromorphone hydrochloride.

9. The method of claim 1, wherein the dosage form provides a peak plasma level of hydromorphone obtained in-vivo which occurs between 4.8 to 8 hours after administration of the dosage form.

10. The method of claim 8, wherein the dosage form provides a peak plasma level of hydromorphone obtained in-vivo which occurs between 4.8 to 8 hours after administration of the dosage form.

11. The method of claim 1, wherein the dosage form provides a peak plasma level of hydromorphone obtained in-vivo which occurs between 5.5 to 8 hours after administration of the dosage form.

12. The method of claim 8, wherein the dosage form provides a peak plasma level of hydromorphone obtained in-vivo which occurs between 5.5 to 8 hours after administration of the dosage form.

13. The method of claim 1, wherein the dosage form provides the mean $C_{max}$ of hydromorphone of 1211±153 pg/ml.

14. The method of claim 1, wherein the dosage form provides a mean $C_{24}$ of hydromorphone of about 600 pg/ml.

15. The method of claim 8, wherein the dosage form provides the mean $C_{max}$ of hydromorphone of 1211±153 pg/ml.

16. The method of claim 8, wherein the dosage form provides a mean $C_{24}$ of hydromorphone of about 600 pg/ml.

17. A method for treating pain in humans for a time period of about 24 hours, comprising administering to a human patient at a dosing interval of about 24 hours a solid, controlled-release oral dosage form comprising 8 to 64 mg of hydromorphone or a pharmaceutically acceptable salt thereof incorporated into a controlled-release formulation comprising a tablet overcoated with a controlled-release coating derived from an aqueous dispersion of a hydrophobic polymer selected from the group consisting of a cellulosic polymer, an acrylic polymer, and mixtures thereof, and a barrier coating separating hydromorphone from the controlled-release coating, wherein (i) the dissolution rate in vitro of the dosage form, when measured by the USP Paddle Method of U.S. Pharmacopeia XXII (1990) at 100 rpm at 900 ml aqueous buffer at pH 1.6 and 7.2 and at 37° C., is such that from 12.5% to 42.5% (by wt) hydromorphone is released after 1 hour, from 25% to 65% (by wt) hydromorphone is released after 2 hours, from 45% to 85% (by wt) hydromorphone is released after 4 hours and greater than 60% (by wt) hydromorphone is released after 8 hours, and (ii) the in-vitro release rate is substantially independent of pH in that a difference, at any given time, between an amount of hydromorphone released at one pH and an amount released at any other pH, when measured in-vitro using the USP Paddle Method of U.S. Pharmacopeia XXII (1990) at 100 rpm in 900 ml aqueous buffer is no greater than 10%, the dosage form providing a duration of therapeutic effect of at least 24 hours, a mean $C_{max}$ of hydromorphone of from about 1070 pg/ml to about 1721 pg/ml and a $T_{max}$ of between 4.4 and 8 hours, based on a single dose administration of the dosage form comprising 8 mg of hydromorphone hydrochloride.

18. The method of claim 17, wherein the dosage form provides a mean $C_{max}$ of 1211±153 pg/ml.

19. A method for treating pain in humans for a time period of about 24 hours, comprising administering to a human patient at a dosing interval of about 24 hours a solid, controlled-release oral dosage form comprising an active agent consisting essentially of 8 to 64 mg of hydromorphone or a pharmaceutically acceptable salt thereof incorporated into a controlled-release formulation comprising a tablet overcoated with a controlled-release coating derived from an aqueous dispersion of a hydrophobic polymer selected from the group consisting of a cellulosic polymer, an acrylic polymer, and mixtures thereof, wherein the coating has been stabilized by curing for about 24 hours or more at a temperature greater than the glass transition temperature of the hydrophobic polymer and at a relative humidity from about 60% to about 100% such that the dosage form attains a dissolution profile which is substantially unaffected by exposure to storage conditions of at least one month at a temperature of 40° C. and a relative humidity of 75%, wherein (i) the dissolution rate in vitro of the dosage form, when measured by the USP Paddle Method of U.S. Pharmacopeia XXII (1990) at 100 rpm at 900 ml aqueous buffer at pH 1.6 and 7.2 and at 37° C., is such that from 12.5% to 42.5% (by wt) hydromorphone released after 1 hour, from 25% to 65% (by wt) hydromorphone released after 2 hours, from 45% to 85% (by wt) hydromorphone released after 4 hours and greater than 60% (by wt) hydromorphone released after 8 hours, and (ii) the in-vitro release rate is substantially independent of pH in that a difference, at any given time, between an amount of hydromorphone released at one pH and an amount released at any other pH, when measured in-vitro using the USP Paddle Method of U.S. Pharmacopeia XXII (1990) at 100 rpm in 900 ml aqueous buffer is no greater than 10%, the dosage form providing a duration of therapeutic effect of at least 24 hours, a mean $C_{max}$ of hydromorphone from about 1070 pg/ml to about 1721 pg/ml and a $T_{max}$ of between 4.4 to 8 hours, based on a single dose administration of the dosage form comprising 8 mg of hydromorphone hydrochloride.

20. The method of claim 19, wherein the dosage form provides a mean $C_{max}$ of hydromorphone of 1211±153 pg/ml.

21. The method of claim 1, wherein the controlled-release formulation further comprises a barrier coating separating hydromorphone from the controlled-release coating.

22. The method of claim 8, wherein the controlled-release formulation further comprises a barrier coating separating hydromorphone from the controlled-release coating.

23. The method of claim 19, wherein the controlled-release formulation further comprises a barrier coating separating hydromorphone from the controlled-release coating.

* * * * *